(12) United States Patent
Wale et al.

(10) Patent No.: US 8,162,847 B2
(45) Date of Patent: Apr. 24, 2012

(54) MRI BIOPSY TARGETING CUBE WITH SNAP CORNERS

(75) Inventors: Nitin P. Wale, Maharashtra (IN); Santosh G. Deshmukh, Maharashtra (IN); Anil R. Jadhav, Maharashtra (IN); Ajay D. Pawar, Maharashtra (IN); Abhijit G. Kulkarni, Maharashtra (IN); John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 448 days.

(21) Appl. No.: 12/580,288

(22) Filed: Oct. 16, 2009

(65) Prior Publication Data

US 2011/0092847 A1 Apr. 21, 2011

(51) Int. Cl.
*A61B 10/00* (2006.01)
*A61B 19/00* (2006.01)

(52) U.S. Cl. ......... 600/562; 600/564; 600/567; 606/130

(58) Field of Classification Search .......... 600/562–572; 606/130
See application file for complete search history.

(56) References Cited

U.S. PATENT DOCUMENTS

| | | | |
|---|---|---|---|
| 5,526,822 A | 6/1996 | Burbank et al. | |
| 5,649,547 A | 7/1997 | Ritchart et al. | |
| 5,769,086 A | 6/1998 | Ritchart et al. | |
| 5,775,333 A | 7/1998 | Burbank et al. | |
| 5,928,164 A | 7/1999 | Burbank et al. | |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,086,544 A | 7/2000 | Hibner et al. | |
| 6,120,462 A | 9/2000 | Hibner et al. | |
| 6,228,055 B1 | 5/2001 | Foerster et al. | |
| 6,231,522 B1 | 5/2001 | Voegele et al. | |
| 6,273,862 B1 | 8/2001 | Privitera et al. | |
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,740,593 B2 * | 6/2010 | Shabaz | 600/562 |
| 7,744,543 B2 * | 6/2010 | Shabaz | 600/562 |

(Continued)

OTHER PUBLICATIONS

U.S. Appl. No. 12/337,814, filed Dec. 18, 2008, Parihar et al.
U.S. Appl. No. 12/337,674, filed Dec. 18, 2008, Parihar et al.
U.S. Appl. No. 12/337,874, filed Dec. 18, 2008, Parihar et al.

(Continued)

*Primary Examiner* — Jeffrey G Hoekstra
(74) *Attorney, Agent, or Firm* — Frost Brown Todd LLC

(57) ABSTRACT

A biopsy system comprises a control module, a localization assembly, a biopsy device, and a targeting cube. The biopsy device and/or other associated components are configured to selectively couple with a targeting cube that selectively couples with a grid plate having apertures for receiving the cube. The targeting cube comprises a body defined by faces. The targeting cube further comprises guide holes that originate and terminate at the faces and pass through the body of the targeting cube to provide passageways through the cube. To securely and removably fit the targeting cube within a grid plate aperture, the targeting cube also comprises deflectable projections positioned at the corners of the cube or extending from the faces of the cube. The projections are resiliently biased to extend outwardly, and are inwardly deflectable by the walls of a grid plate aperture to secure the targeting cube in position within the aperture.

20 Claims, 22 Drawing Sheets

U.S. PATENT DOCUMENTS

| | | |
|---|---|---|
| 2003/0199753 A1 | 10/2003 | Hibner et al. |
| 2005/0283069 A1 | 12/2005 | Hughes et al. |
| 2007/0135821 A1* | 6/2007 | Shabaz .................. 606/130 |
| 2007/0255168 A1 | 11/2007 | Hibner et al. |
| 2007/0255170 A1* | 11/2007 | Hibner et al. .......... 600/564 |
| 2008/0132912 A1* | 6/2008 | Shabaz .................. 606/130 |
| 2008/0146962 A1 | 6/2008 | Ritchie et al. |
| 2008/0214955 A1 | 9/2008 | Speeg et al. |
| 2008/0221480 A1 | 9/2008 | Hibner et al. |
| 2008/0228103 A1 | 9/2008 | Ritchie et al. |

OTHER PUBLICATIONS

U.S. Appl. No. 12/337,911, filed Dec. 18, 2008, Parihar et al.
U.S. Appl. No. 12/337,942, filed Dec. 18, 2008, Parihar et al.
U.S. Appl. No. 12/485,119, filed Jun. 16, 2009, Leimbach et al.
U.S. Appl. No. 12/485,138, filed Jun. 16, 2009, Leimbach et al.
U.S. Appl. No. 12/485,168, filed Jun. 16, 2009, Leimbach et al.
U.S. Appl. No. 12/485,278, filed Jun. 16, 2009, Leimbach et al.
U.S. Appl. No. 12/485,318, filed Jun. 16, 2009, Leimbach.

* cited by examiner

MRI BIOPSY TARGETING CUBE WITH SNAP CORNERS

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 6,273,862, entitled "Surgical Device for the Collection of Soft Tissue," issued Aug. 14, 2001; U.S. Pat. No. 6,231,522, entitled "Biopsy Instrument with Breakable Sample Segments," issued May 15, 2001; U.S. Pat. No. 6,228,055, entitled "Devices for Marking and Defining Particular Locations in Body Tissue," issued May 8, 2001; U.S. Pat. No. 6,120,462, entitled "Control Method for an Automated Surgical Biopsy Device," issued Sep. 19, 2000; U.S. Pat. No. 6,086,544, entitled "Control Apparatus for an Automated Surgical Biopsy Device," issued Jul. 11, 2000; U.S. Pat. No. 6,077,230, entitled "Biopsy Instrument with Removable Extractor," issued Jun. 20, 2000; U.S. Pat. No. 6,017,316, entitled "Vacuum Control System and Method for Automated Biopsy Device," issued Jan. 25, 2000; U.S. Pat. No. 6,007,497, entitled "Surgical Biopsy Device," issued Dec. 28, 1999; U.S. Pat. No. 5,980,469, entitled "Method and Apparatus for Automated Biopsy and Collection of Soft Tissue," issued Nov. 9, 1999; U.S. Pat. No. 5,964,716, entitled "Method of Use for a Multi-Port Biopsy Instrument," issued Oct. 12, 1999; U.S. Pat. No. 5,928,164, entitled "Apparatus for Automated Biopsy and Collection of Soft Tissue," issued Jul. 27, 1999; U.S. Pat. No. 5,775,333, entitled "Apparatus for Automated Biopsy and Collection of Soft Tissue," issued Jul. 7, 1998; U.S. Pat. No. 5,769,086, entitled "Control System and Method for Automated Biopsy Device," issued Jun. 23, 1998; U.S. Pat. No. 5,649,547, entitled "Methods and Devices for Automated Biopsy and Collection of Soft Tissue," issued Jul. 22, 1997; U.S. Pat. No. 5,526,822, entitled "Method and Apparatus for Automated Biopsy and Collection of Soft Tissue," issued Jun. 18, 1996; U.S. Pub. No. 2008/0214955, entitled "Presentation of Biopsy Sample by Biopsy Device," published Sep. 4, 2008; U.S. Pub. No. 2007/0255168, entitled "Grid and Rotatable Cube Guide Localization Fixture for Biopsy Device," published Nov. 1, 2007; U.S. Pub. No. 2007/0118048, entitled "Remote Thumbwheel for a Surgical Biopsy Device," published May 24, 2007; U.S. Pub. No. 2005/0283069, entitled "MRI Biopsy Device Localization Fixture," published Dec. 22, 2005; U.S. Pub. No. 2003/0199753, entitled "MRI Compatible Biopsy Device with Detachable Probe," published Oct. 23, 2003; U.S. Pub. No. 2003/0109803, entitled "MRI Compatible Surgical Biopsy Device," published Jun. 12, 2003; U.S. Pub. No. 2008/0221480, entitled "Biopsy Sample Storage," published Sep. 11, 2008; and U.S. Pub. No. 2008/0146962, entitled "Biopsy System with Vacuum Control Module," published Jun. 19, 2008. The disclosure of each of the above-cited U.S. patents and U.S. patent application Publications is incorporated by reference herein.

Some biopsy systems may provide an apparatus to guide a probe and/or other components of a biopsy device to a desired biopsy site. In some such biopsy systems, a guide cube and positioning grid plate may be used. The guide cube may be selectively located within an opening in the grid plate. The guide cube may include guide holes to receive a portion of the probe and/or other components, for example a needle, cannula, obturator, or combinations of these or other components. With the guide cube inserted in the grid plate, the probe or other components can be guided through a selected guide hole of the guide cube to arrive at a desired biopsy site. The desired biopsy site may or may not have been identified and/or targeted by one or more of the guidance approaches mentioned above. In some situations, it might be desirable to provide a guide cube with features that improve a guide cube's use with one or more positioning grid plates. Merely exemplary biopsy device guides are disclosed in U.S. patent application Ser. No. 12/485,119, entitled "Biopsy Targeting Cube with Elastomeric Edges," filed Jun. 16, 2009; U.S. patent application Ser. No. 12/485,138, entitled "Biopsy Targeting Cube with Elastomeric Body," filed Jun. 16, 2009; U.S. patent application Ser. No. 12/485,168, entitled "Biopsy Targeting Cube with Malleable Members," filed Jun. 16, 2009; U.S. patent application Ser. No. 12/485,278, entitled "Biopsy Targeting Cube with Angled Interface," filed Jun. 16, 2009; and U.S. patent application Ser. No. 12/485,318, entitled "Biopsy Targeting Cube with Living Hinges," filed Jun. 16, 2009. The disclosure of each of the above-cited U.S. patent applications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
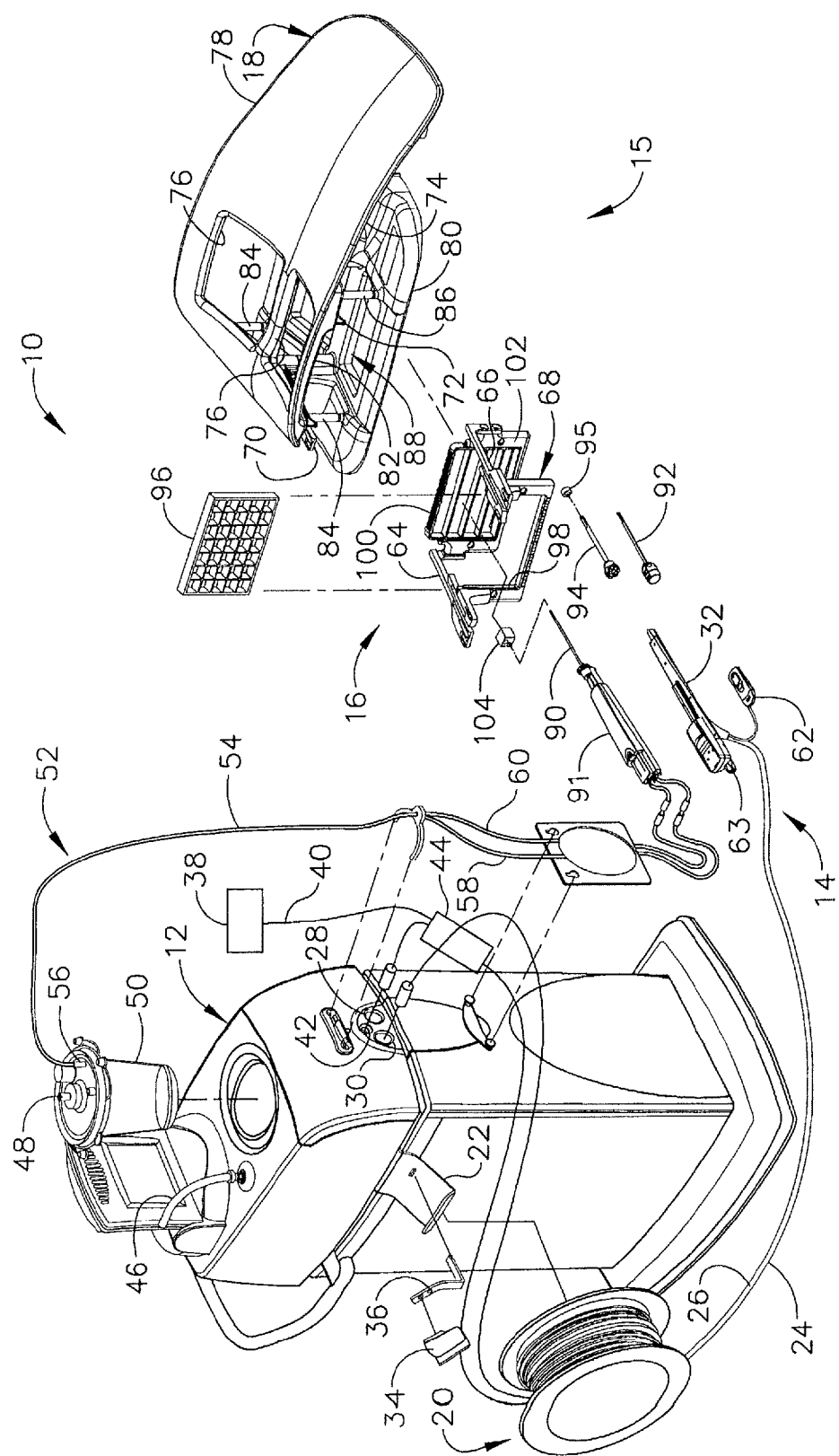
FIG. 1 is a perspective view of a biopsy system including a control module remotely coupled to a biopsy device, and including a localization assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

As shown in the figures, an exemplary magnetic resonance imaging (MRI or MR imaging) compatible biopsy system may include a control module (12), localization assembly (15), and biopsy device (14). In particular, localization assembly (15) is configured to localize a patient's breast and guide needle (90) of biopsy device (14) to a targeted area within the patient's breast; while control module (12) is operable to control biopsy device (14) after needle (90) has been introduced to the target site. These components and their sub-components will be discussed further below. In addition, guide cubes for use with various localization assemblies will be discussed. While this disclosure may reference the biopsy system as compatible with MRI and MRI equipment and devices, it should be appreciated that other imaging techniques and equipment and devices may be used with the components described below, including but not limited to stereotactic, ultrasound, PEM, BSGI, and/or other imaging techniques and equipment.

I. Control Module

Figure 2:
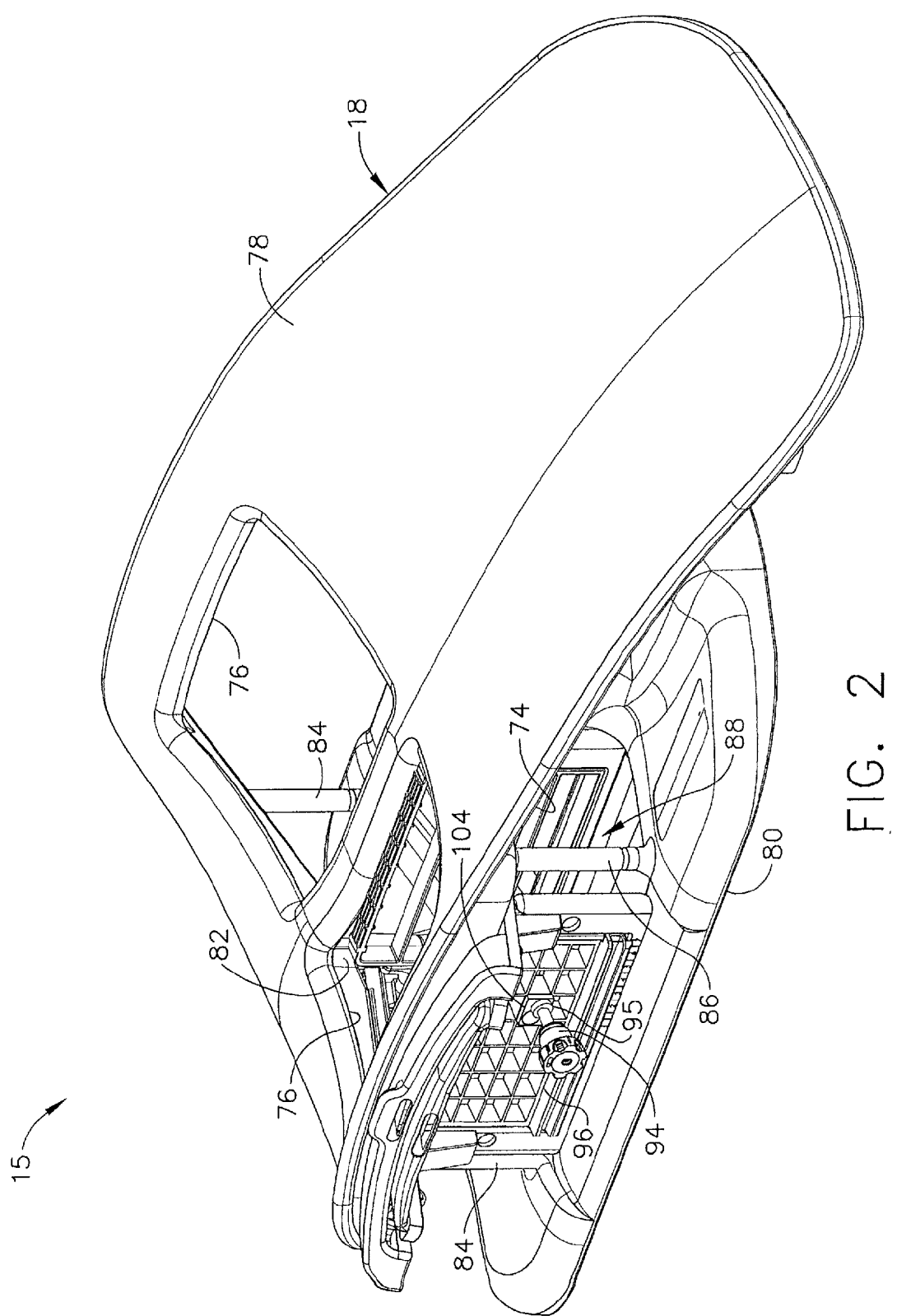
FIG. 2 is a perspective view of a breast coil of the localization assembly of FIG. 1.
Figure 3:
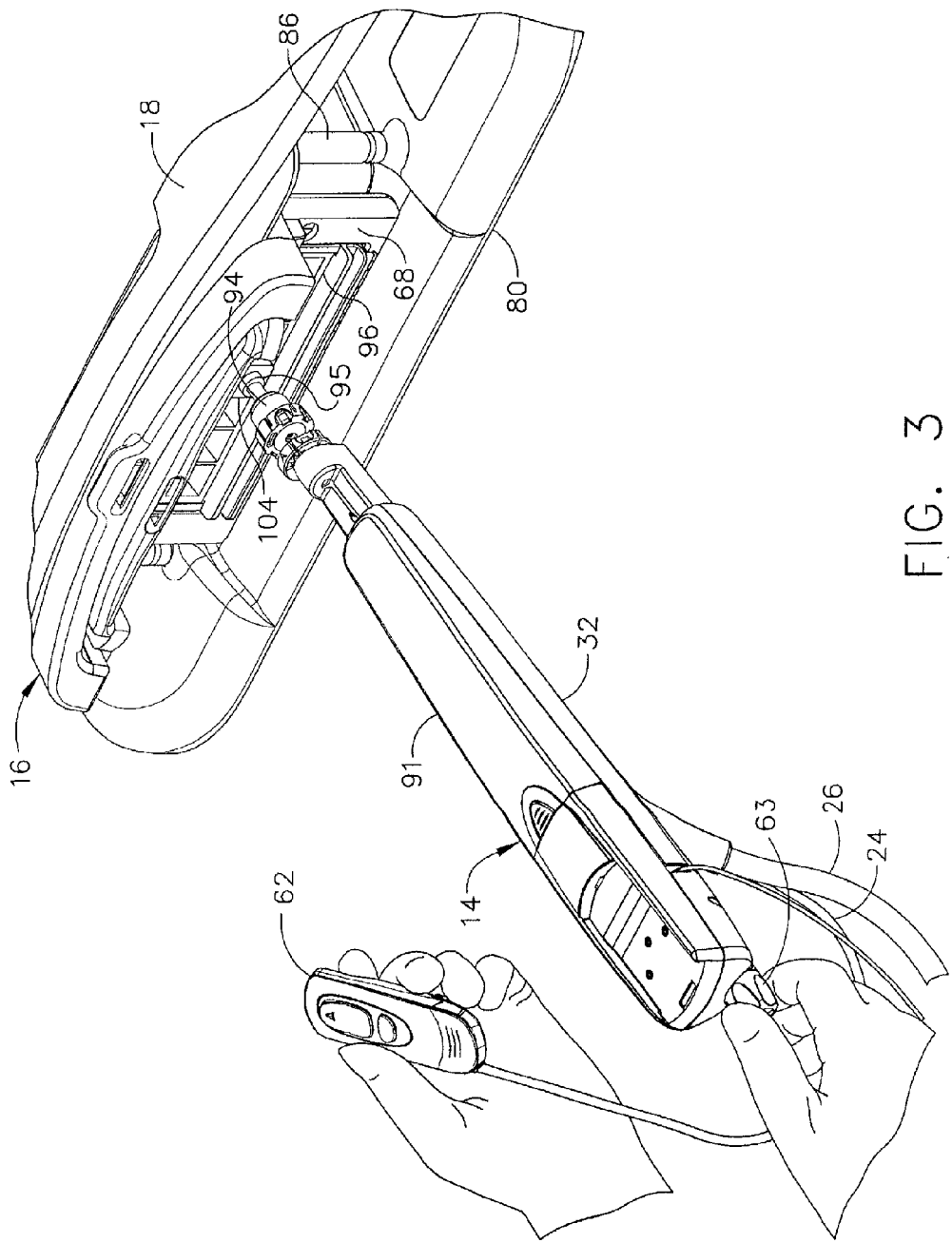
FIG. 3 is a perspective view of the biopsy device inserted through the guide cube of the localization assembly of FIG. 1.

In FIGS. 1-3, MRI compatible biopsy system (10) has control module (12) that may be placed outside of a shielded room containing an MRI machine (not shown) or at least spaced away to mitigate detrimental interaction with its strong magnetic field and/or sensitive radio frequency (RF) signal detection antennas. As described in U.S. Pat. No. 6,752,768, which is hereby incorporated by reference in its entirety, a range of preprogrammed functionality may be incorporated into control module (12) to assist in taking tissue samples. Control module (12) controls and powers biopsy device (14) that is used with localization assembly (15). Biopsy device (14) is positioned and guided by localization fixture (16) attached to breast coil (18) that may be placed upon a gantry (not shown) of a MRI or other imaging machine.

In the present example, control module (12) is mechanically, electrically, and pneumatically coupled to biopsy device (14) so that components may be segregated that need to be spaced away from the strong magnetic field and the sensitive RF receiving components of a MRI machine. Cable management spool (20) is placed upon cable management attachment saddle (22) that projects from a side of control module (12). Wound upon cable management spool (20) is paired electrical cable (24) and mechanical cable (26) for communicating control signals and cutter rotation/advancement motions respectively. In particular, electrical and mechanical cables (24, 26) each have one end connected to respective electrical and mechanical ports (28, 30) in control module (12) and another end connected to holster portion (32) of biopsy device (14). Docking cup (34), which may hold holster portion (32) when not in use, is hooked to control module (12) by docking station mounting bracket (36). It should be understood that such components described above as being associated with control module (12) are merely optional.

Interface lock box (38) mounted to a wall provides tether (40) to lockout port (42) on control module (12). Tether (40) is uniquely terminated and of short length to preclude inadvertent positioning of control module (12) too close to a MRI machine or other machine In-line enclosure (44) may register tether (40), electrical cable (24) and mechanical cable (26) to their respective ports (42, 28, 30) on control module (12).

Vacuum assist is provided by first vacuum line (46) that connects between control module (12) and outlet port (48) of vacuum canister (50) that catches liquid and solid debris. Tubing kit (52) completes the pneumatic communication between control module (12) and biopsy device (14). In particular, second vacuum line (54) is connected to inlet port (56) of vacuum canister (50). Second vacuum line (54) divides into two vacuum lines (58, 60) that are attached to biopsy device (14). With biopsy device (14) installed in holster portion (32), control module (12) performs a functional check. Saline may be manually injected into biopsy device (14) or otherwise introduced to biopsy device (14), such as to serve as a lubricant and to assist in achieving a vacuum seal and/or for other purposes. Control module (12) actuates a cutter mechanism (not shown) in biopsy device (14), monitoring full travel of a cutter in biopsy device (14) in the present example. Binding in mechanical cable (26) or within biopsy device (14) may optionally monitored with reference to motor force exerted to turn mechanical cable (26) and/or an amount of twist in mechanical cable (26) sensed in comparing rotary speed or position at each end of mechanical cable (26).

Remote keypad (62), which is detachable from holster portion (32), communicates via electrical cable (24) to control panel (12) to enhance clinician control of biopsy device

(14) in the present example, especially when controls that would otherwise be on biopsy device (14) itself are not readily accessible after insertion into localization fixture (16) and/or placement of control module (12) is inconveniently remote (e.g., 30 feet away). However, as with other components described herein, remote keypad (62) is merely optional, and may be modified, substituted, supplemented, or omitted as desired. In the present example, aft end thumbwheel (63) on holster portion (32) is also readily accessible after insertion to rotate the side from which a tissue sample is to be taken.

Of course, the above-described control module (12) is merely one example. Any other suitable type of control module (12) and associated components may be used. By way of example only, control module (12) may instead be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. As another merely illustrative example, control module (12) may instead be configured and operable in accordance with the teachings of U.S. patent application Ser. No. 12/337,814, entitled "Control Module Interface for MRI Biopsy Device," filed Dec. 18, 2008, the disclosure of which is incorporated by reference herein. Alternatively, control module (12) may have any other suitable components, features, configurations, functionalities, operability, etc. Other suitable variations of control module (12) and associated components will be apparent to those of ordinary skill in the art in view of the teachings herein.

II. Localization Assembly

Localization assembly (15) of the present example comprises breast coil (18) and localization fixture (16). These components of localization assembly (15) are described further below.

Left and right parallel upper guides (64, 66) of localization framework (68) are laterally adjustably received respectively within left and right parallel upper tracks (70, 72) attached to under side (74) and to each side of a selected breast aperture (76) formed in patient support platform (78) of breast coil (18). Base (80) of breast coil (18) is connected by centerline pillars (82) that are attached to patient support platform (78) between breast apertures (76). Also, a pair of outer vertical support pillars (84, 86) on each side spaced about a respective breast aperture (76) respectively define lateral recess (88) within which localization fixture (16) resides.

It should be appreciated that the patient's breasts hang pendulously respectively into breast apertures (76) within lateral recesses (88) in the present example. For convenience, herein a convention is used for locating a suspicious lesion by Cartesian coordinates within breast tissue referenced to localization fixture (16) and to thereafter selectively position an instrument, such as needle (90) of probe (91) that is engaged to holster portion (32) to form biopsy device (14). Of course, any other type of coordinate system or targeting techniques may be used. To enhance hands-off use of biopsy system (10), especially for repeated re-imaging within the narrow confines of a closed bore MRI machine, biopsy system (10) may also guide obturator (92) encompassed by cannula (94). Depth of insertion is controlled by depth stop device (95) longitudinally positioned on either needle (90) or cannula (94). Alternatively, depth of insertion may be controlled in any other suitable fashion.

This guidance is specifically provided by a lateral fence in the present example, depicted as grid plate (96), which is received within laterally adjustable outer three-sided plate bracket (98) attached below left and right parallel upper guides (64, 66). Similarly, a medial fence with respect to a medial plane of the chest of the patient, depicted as medial plate (100), is received within inner three-sided plate bracket (102) attached below left and right parallel upper guides (64, 66) close to centerline pillars (82) when installed in breast coil (18). To further refine the insertion point of the instrument (e.g., needle (90) of probe (91), obturator/cannula (92, 94), etc.), guide cube (104) may be inserted into grid plate (96).

In the present example, the selected breast is compressed along an inner (medial) side by medial plate (100) and on an outer (lateral) side of the breast by grid plate (96), the latter defining an X-Y plane. The X-axis is vertical (sagittal) with respect to a standing patient and corresponds to a left-to-right axis as viewed by a clinician facing the externally exposed portion of localization fixture (16). Perpendicular to this X-Y plane extending toward the medial side of the breast is the Z-axis, which typically corresponds to the orientation and depth of insertion of needle (90) or obturator/cannula (92, 94) of biopsy device (14). For clarity, the term Z-axis may be used interchangeably with "axis of penetration", although the latter may or may not be orthogonal to the spatial coordinates used to locate an insertion point on the patient. Versions of localization fixture (16) described herein allow a non-orthogonal axis of penetration to the X-Y axis to a lesion at a convenient or clinically beneficial angle.

It should be understood that the above-described localization assembly (15) is merely one example. Any other suitable type of localization assembly (15) may be used, including but not limited to localization assemblies (15) that use a breast coil (18) and/or localization fixture (16) different from those described above. Other suitable components, features, configurations, functionalities, operability, etc. for a localization assembly (15) will be apparent to those of ordinary skill in the art in view of the teachings herein.

III. Biopsy Device

As shown in FIG. 1, one version of biopsy device (14) may comprise holster portion (32) and probe (91). Exemplary holster portion (32) was discussed previously in the above section addressing control module (12). The following paragraphs will discuss probe (91) and associated components and devices in further detail.

Figure 4:
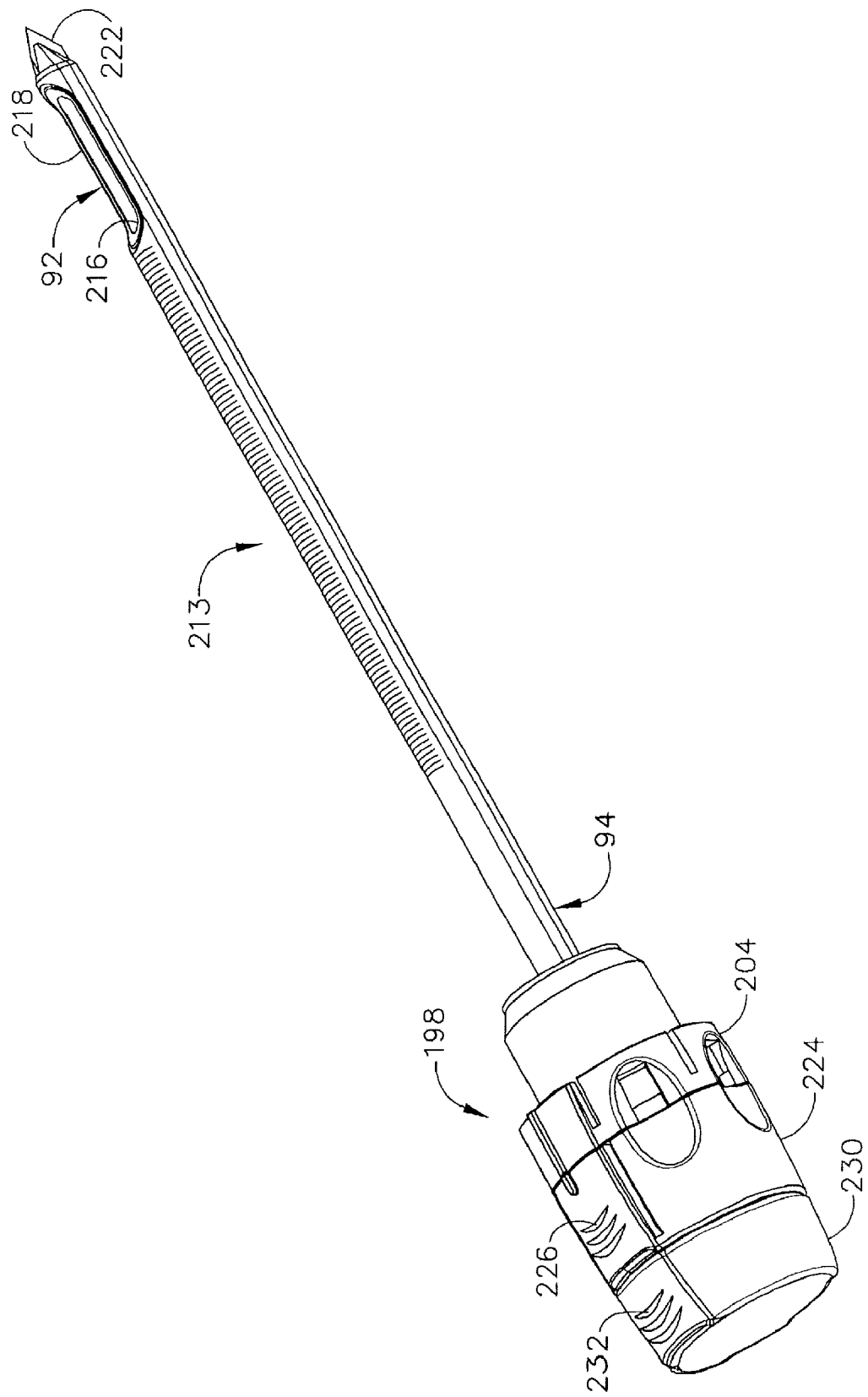
FIG. 4 is a perspective view of the obturator and cannula of the biopsy system of FIG. 1.
Figure 5:
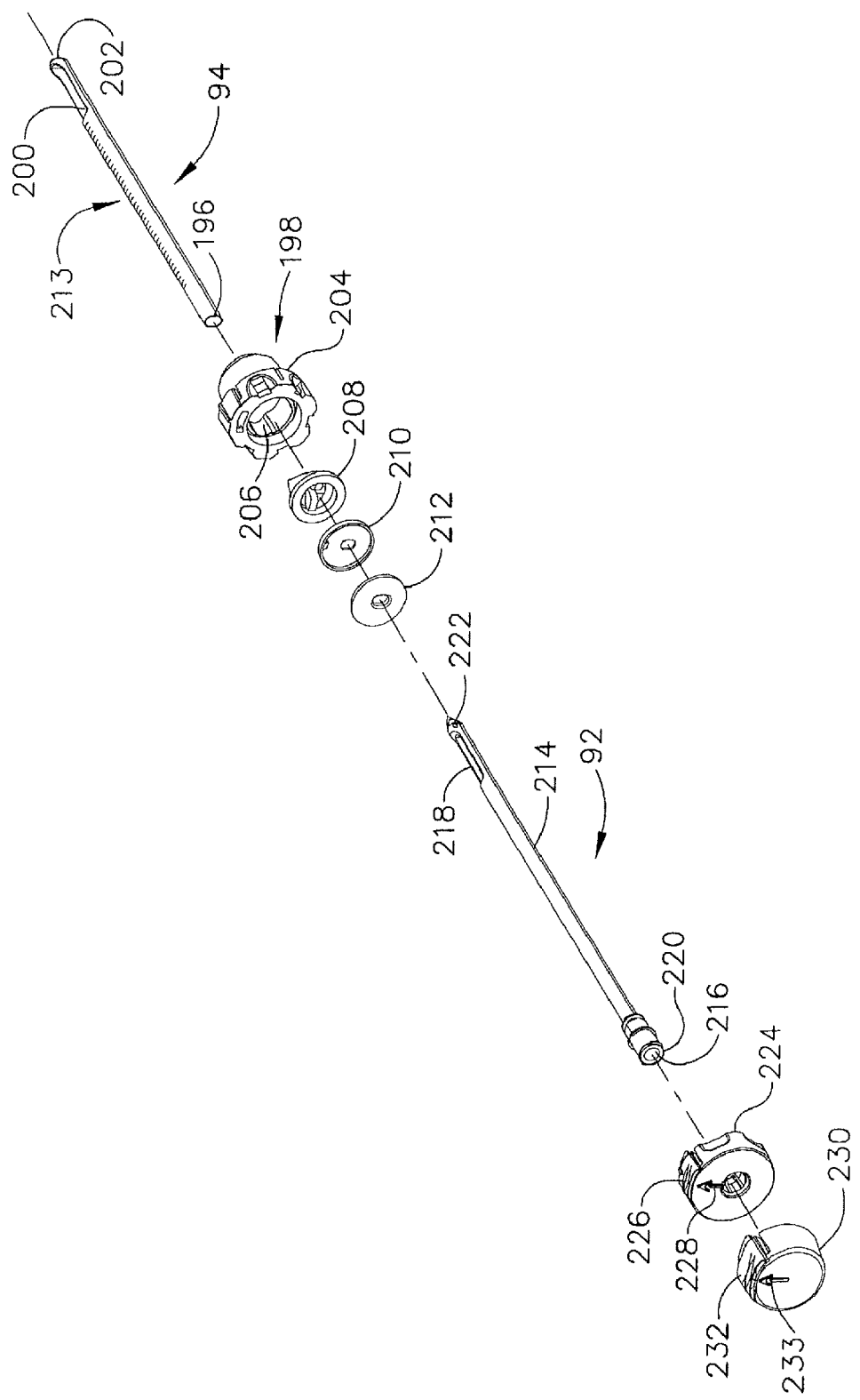
FIG. 5 is an exploded perspective view of the obturator and cannula of FIG. 4.
Figure 7:
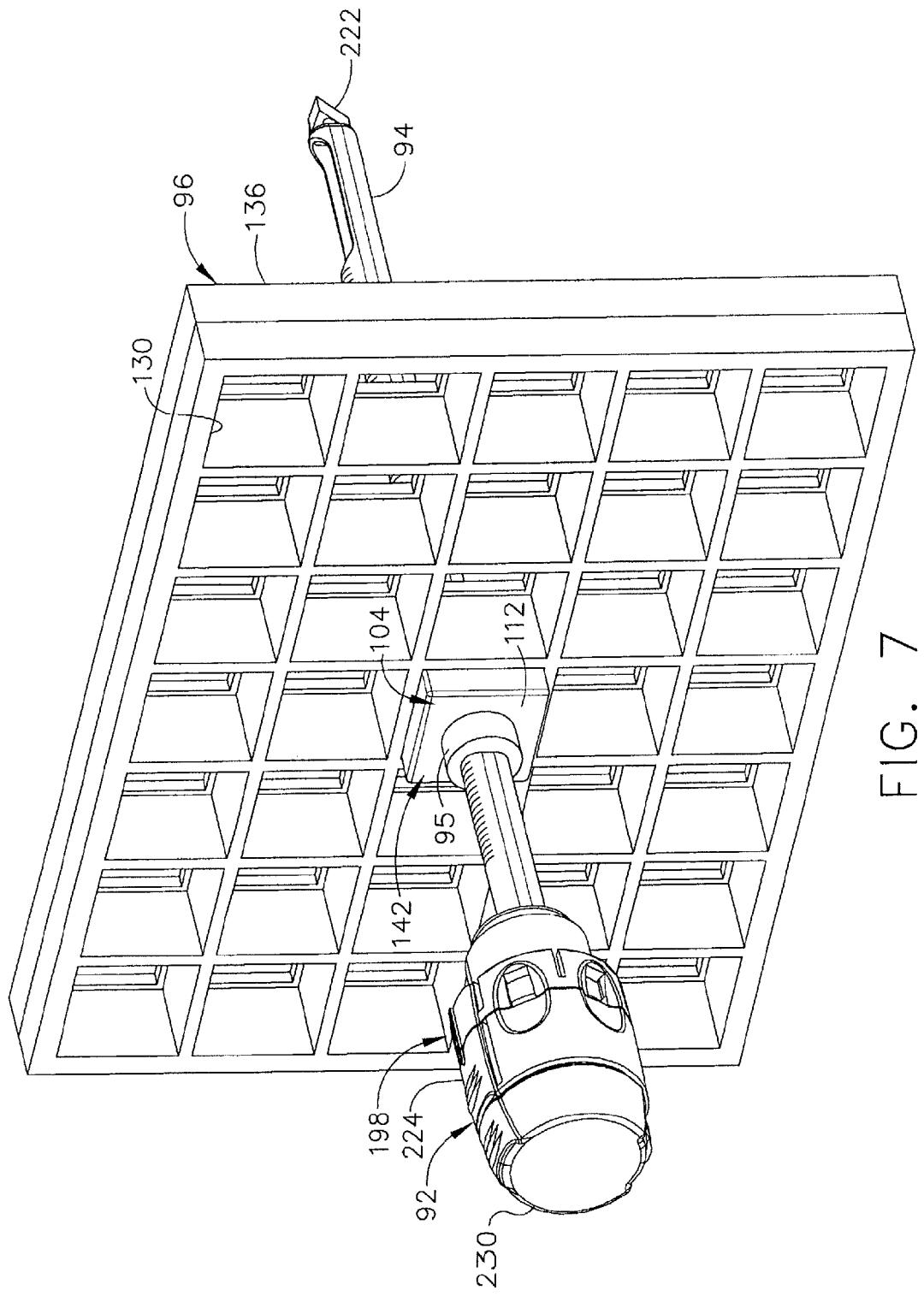
FIG. 7 is a perspective view of the obturator and cannula of FIG. 4 with a depth stop device of FIG. 1 inserted through the guide cube and grid plate of FIG. 6.

In the present example, cannula (94) and obturator (92) are associated with probe (91). In particular, and as shown in FIGS. 4, 5, and 7, obturator (92) is slid into cannula (94) and the combination is guided through guide cube (104) to the biopsy site within the breast tissue. Obturator (92) is then withdrawn from cannula (94), then needle (90) of probe (91) is inserted in cannula (94), and then biopsy device (14) is operated to acquire one or more tissue samples from the breast via needle (90).

Cannula (94) of the present example is proximally attached to cylindrical hub (198) and cannula (94) includes lumen (196) and lateral aperture (200) proximate to open distal end (202). Cylindrical hub (198) has exteriorly presented thumbwheel (204) for rotating lateral aperture (200). Cylindrical hub (198) has interior recess (206) that encompasses duckbill seal (208), wiper seal (210) and seal retainer (212) to provide a fluid seal when lumen (196) is empty and for sealing to inserted obturator (92). Longitudinally spaced measurement indicia (213) along an outer surface of cannula (94) visually, and perhaps physically, provide a means to locate depth stop device (95) of FIG. 1.

Obturator (92) of the present example incorporates a number of components with corresponding features. Hollow shaft (214) includes fluid lumen (216) that communicates between imageable side notch (218) and proximal port (220). Hollow shaft (214) is longitudinally sized to extend, when fully engaged with cannula (94), piercing tip (222) out of distal end (202) of cannula (94). Obturator thumbwheel cap (224) encompasses proximal port (220) and includes locking feature (226), which includes visible angle indicator (228), that engages cannula thumbwheel (204) to ensure that imageable side notch (218) is registered to lateral aperture (200) in cannula (94). Obturator seal cap (230) may be engaged proximally into obturator thumbwheel cap (224) to close fluid lumen (216). Obturator seal cap (230) of the present example includes locking or locating feature (232) that includes visible angle indicator (233) that corresponds with visible angle indicator (228) on obturator thumbwheel cap (224), which may be fashioned from either a rigid, soft, or elastomeric material. In FIG. 7, guide cube (104) has guided obturator (92) and cannula (94) through grid plate (96).

While obturator (92) of the present example is hollow, it should be understood that obturator (92) may alternatively have a substantially solid interior, such that obturator (92) does not define an interior lumen. In addition, obturator (92) may lack side notch (218) in some versions. Other suitable components, features, configurations, functionalities, operability, etc. for an obturator (92) will be apparent to those of ordinary skill in the art in view of the teachings herein. Likewise, cannula (94) may be varied in a number of ways. For instance, in some other versions, cannula (94) has a closed distal end (202). As another merely illustrative example, cannula (94) may have a closed piercing tip (222) instead of obturator (92) having piercing tip (222). In some such versions, obturator (92) may simply have a blunt distal end; or the distal end of obturator (92) may have any other suitable structures, features, or configurations. Other suitable components, features, configurations, functionalities, operability, etc. for a cannula (94) will be apparent to those of ordinary skill in the art in view of the teachings herein. Furthermore, in some versions, one or both of obturator (92) or cannula (94) may be omitted altogether. For instance, needle (90) of probe (91) may be directly inserted into a guide cube (104), without being inserted into guide cube (104) via cannula (94).

Another component that may be used with probe (91) (or needle (90)) is depth stop (95). Depth stop may be of any suitable configuration that is operable to prevent cannula (94) and obturator (92) (or needle (90)) from being inserted further than desired. For instance, depth stop (95) may be positioned on the exterior of cannula (94) (or needle (90)), and may be configured to restrict the extent to which cannula (94) is inserted into a guide cube. It should be understood that such restriction by depth stop (95) may further provide a limit on the depth to which the combination of cannula (94) and obturator (92) (or needle (90)) may be inserted into the patient's breast. Furthermore, it should be understood that such restriction may establish the depth within the patient's breast at which biopsy device (14) acquires one or more tissue samples after obturator (92) has been withdrawn from cannula (94) and needle (90) has been inserted in cannula (94). Exemplary depth stops (95) that may be used with biopsy system (10) are described in U.S. Pub. No. 2007/0255168, entitled "Grid and Rotatable Cube Guide Localization Fixture for Biopsy Device," published Nov. 1, 2007, and incorporated by reference herein as mentioned previously.

In the present example, and as noted above, biopsy device (14) includes a needle (90) that may be inserted into cannula (94) after the combination of cannula (94) and obturator (92) has been inserted to a desired location within a patient's breast and after obturator (92) has been removed from cannula (94). Needle (90) of the present example comprises a lateral aperture (not shown) that is configured to substantially align with lateral aperture (200) of cannula (94) when needle (90) is inserted into lumen (196) of cannula (94). Probe (91) of the present example further comprises a rotating and translating cutter (not shown), which is driven by components in holster (32), and which is operable to sever tissue protruding through lateral aperture (200) of cannula (94) and the lateral aperture of needle (90). Severed tissue samples may be retrieved from biopsy device (14) in any suitable fashion.

By way of example only, biopsy device (14) may be configured and operable in accordance with the teachings of U.S. Pub. No. 2008/0228103, entitled "Vacuum Timing Algorithm For Biopsy Device," published Sep. 18, 2008, the disclosure of which is incorporated by reference herein. As another merely illustrative example, biopsy device (14) may be configured and operable in accordance with the teachings of U.S. patent application Ser. No. 12/337,874, entitled "Mechanical Tissue Sample Holder Indexing Device," filed Dec. 18, 2008, the disclosure of which is incorporated by reference herein. As another merely illustrative example, biopsy device (14) may be configured and operable in accordance with the teachings of U.S. patent application Ser. No. 12/337,674, entitled "Biopsy Device with Sliding Cutter Cover," filed Dec. 18, 2008, the disclosure of which is incorporated by reference herein. By way of example only, cannula (94) may be replaced with any of the detachable needles described in U.S. patent application Ser. No. 12/337,674, entitled "Biopsy Device with Sliding Cutter Cover." As another merely illustrative example, biopsy device (14) may be configured and operable in accordance with the teachings of U.S. patent application Ser. No. 12/337,911, entitled "Biopsy Device with Discrete Tissue Chambers," filed Dec. 18, 2008, the disclosure of which is incorporated by reference herein. As another merely illustrative example, biopsy device (14) may be configured and operable in accordance with the teachings of U.S. patent application Ser. No. 12/337,942, entitled "Biopsy Device with Central Thumbwheel," filed Dec. 18, 2008, the disclosure of which is incorporated by reference herein. Alternatively, biopsy device (14) may have any other suitable components, features, configurations, functionalities, operability, etc. Other suitable variations of biopsy device (14) and associated components will be apparent to those of ordinary skill in the art in view of the teachings herein IV. Guide Cubes Guide cubes described below are generally adapted for use with a localization assembly (15) as described above. Numerous features of merely exemplary guide cubes will be discussed in the paragraphs that follow.

A. Guide Cubes Generally

In some versions, guide cubes may comprise a body defined by one or more edges and faces. The body may include one or more guide holes or other types of passages that extend between faces of the guide cube and that may be used to guide an instrument such as a biopsy device (14) or a portion of a biopsy device (14) (e.g., needle (90) of biopsy device (14), a combination of cannula (94) and obturator (92), etc.). Guide cubes may be rotatable about one, two, or three axes to position the one or more guide holes or passages of the guide cube into a desired position.

Figure 8:
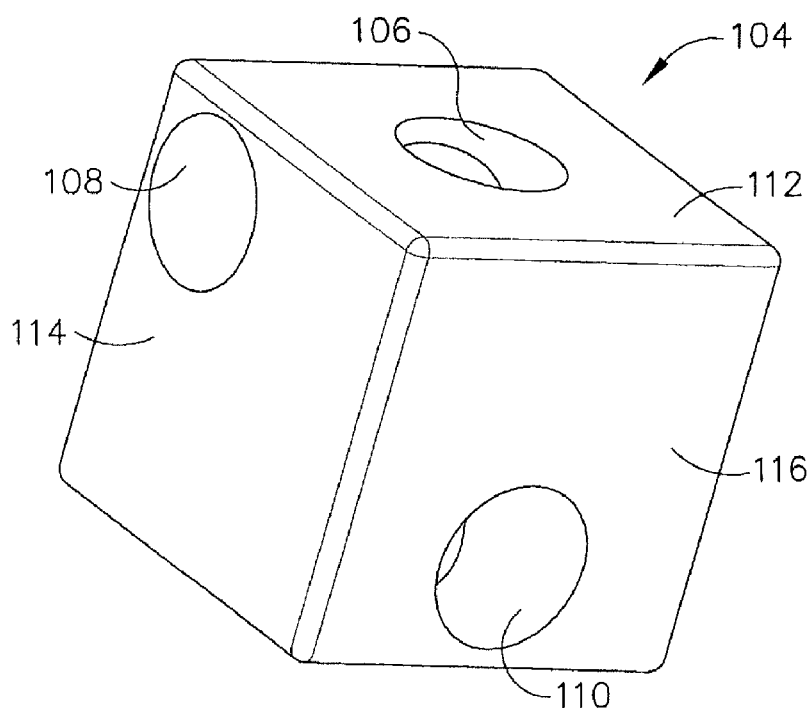
FIG. 8 is a perspective view of the guide cube of the biopsy system of FIG. 1.
Figure 9:
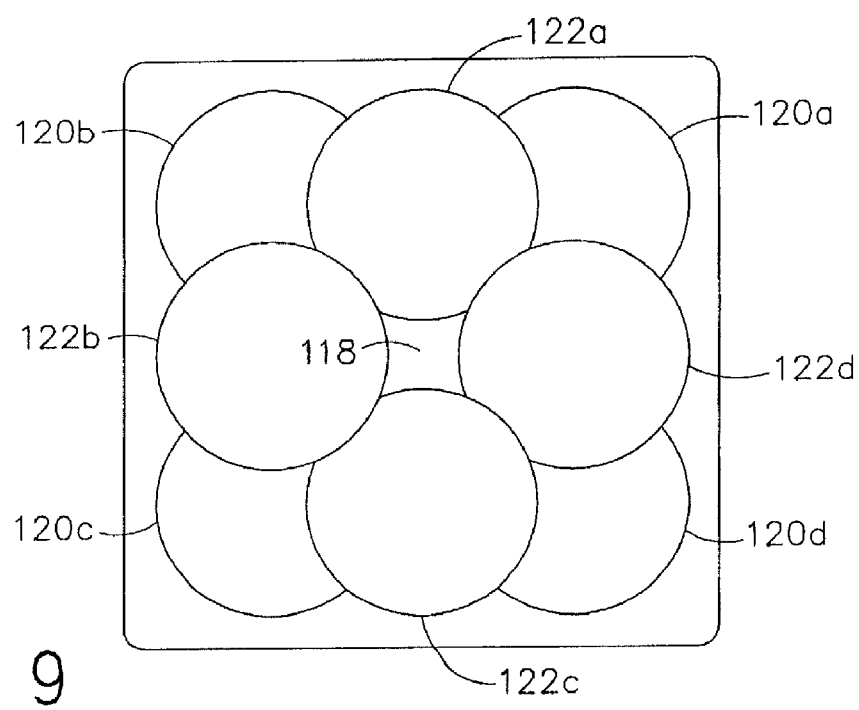
FIG. 9 is a diagram of nine guide positions achievable by rotating the guide cube of FIG. 8.

Referring now to FIG. 8, guide cube (104), includes central guide hole (106), corner guide hole (108), and off-center guide hole (110) that pass orthogonally to one another between respective opposite pairs of faces (112, 114, 116). By selectively rotating guide cube (104) in two axes, one pair of faces (112, 114, 116) may be proximally aligned to an unturned position and then the selected proximal face (112, 114, 116) optionally rotated a quarter turn, half turn, or three-quarter turn. Thereby, one of nine guide positions (118, 120a-120d, 122a-122d) may be proximally exposed as depicted in FIG. 9. More specifically, central guide hole (106) may provide for guide position (118), corner guide hole (108) may provide for guide positions (120a-120d), and off-center guide hole (110) may provide for guide positions (122a-122d).

Figure 6:
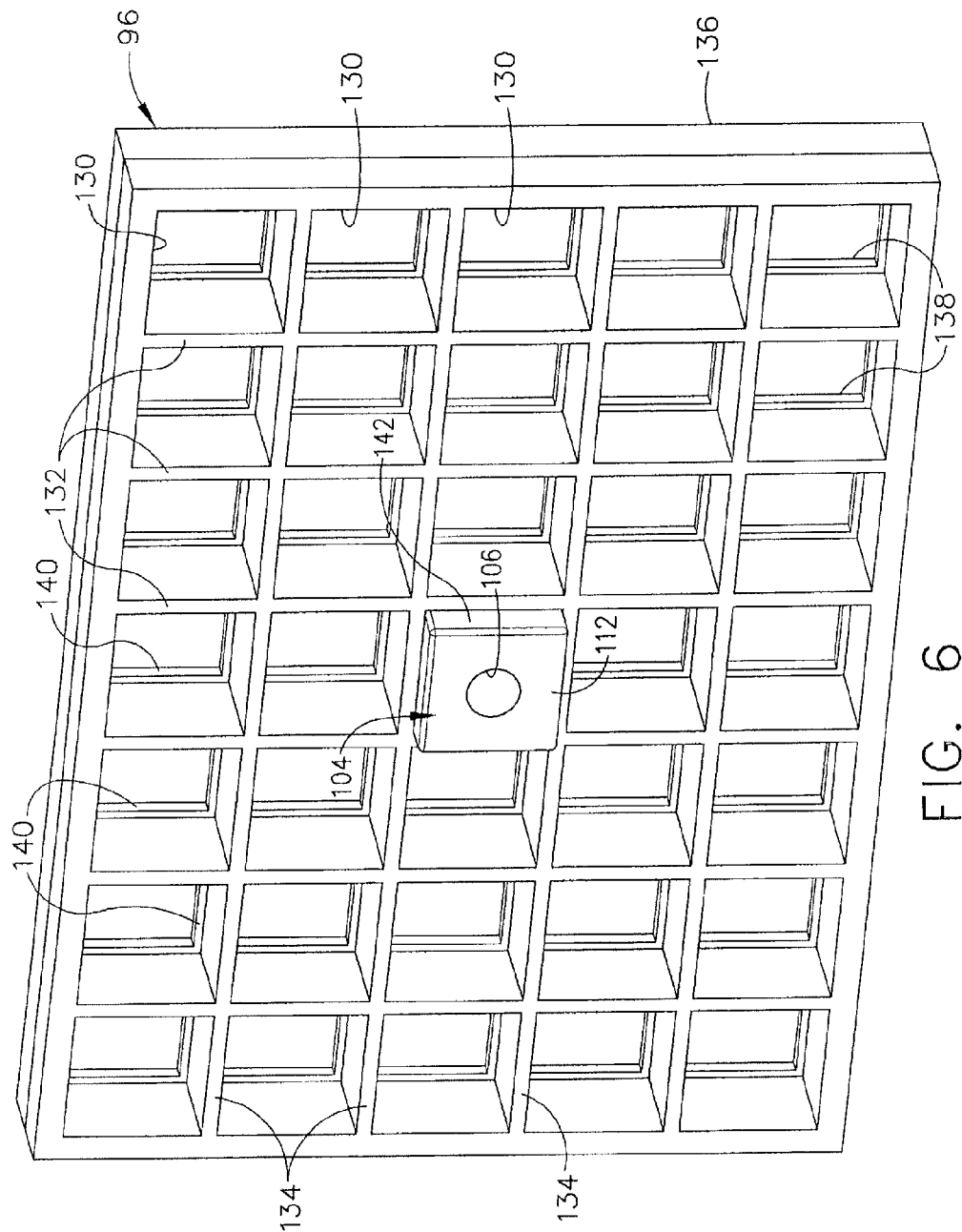
FIG. 6 is a perspective view of the guide cube inserted into the grid plate of the localization assembly of FIG. 1.

In FIG. 6, two-axis rotatable guide cube (104) is sized for insertion from a proximal side into one of a plurality of square recesses (130) in grid plate (96), which are formed by intersecting vertical bars (132) and horizontal bars (134). Guide cube (104) is prevented from passing through grid plate (96) by backing substrate (136) attached to a front face of grid plate (96). Backing substrate (136) includes respective square opening (138) centered within each square recess (130), forming lip (140) sufficient to capture the front face of guide cube (104), but not so large as to obstruct guide holes (104, 106, 108). The depth of square recesses (130) is less than guide cube (104), thereby exposing a proximal portion (142) of guide cube (104) for seizing and extraction from grid plate (96). It will be appreciated by those of ordinary skill in the art based on the teachings herein that backing substrate (136) of grid plate (96) may be omitted altogether in some versions. In some such versions without backing substrate (136) other features of a guide cube, as will be discussed in more detail below, may be used to securely and removably fit a guide cube within a grid plate. However, such other features may also be used in combination with a grid plate having backing substrate (136), such as grid plate (96), instead of partially or wholly omitting backing substrate (136).

B. Self-Grounding Guide Cubes

Figure 10:
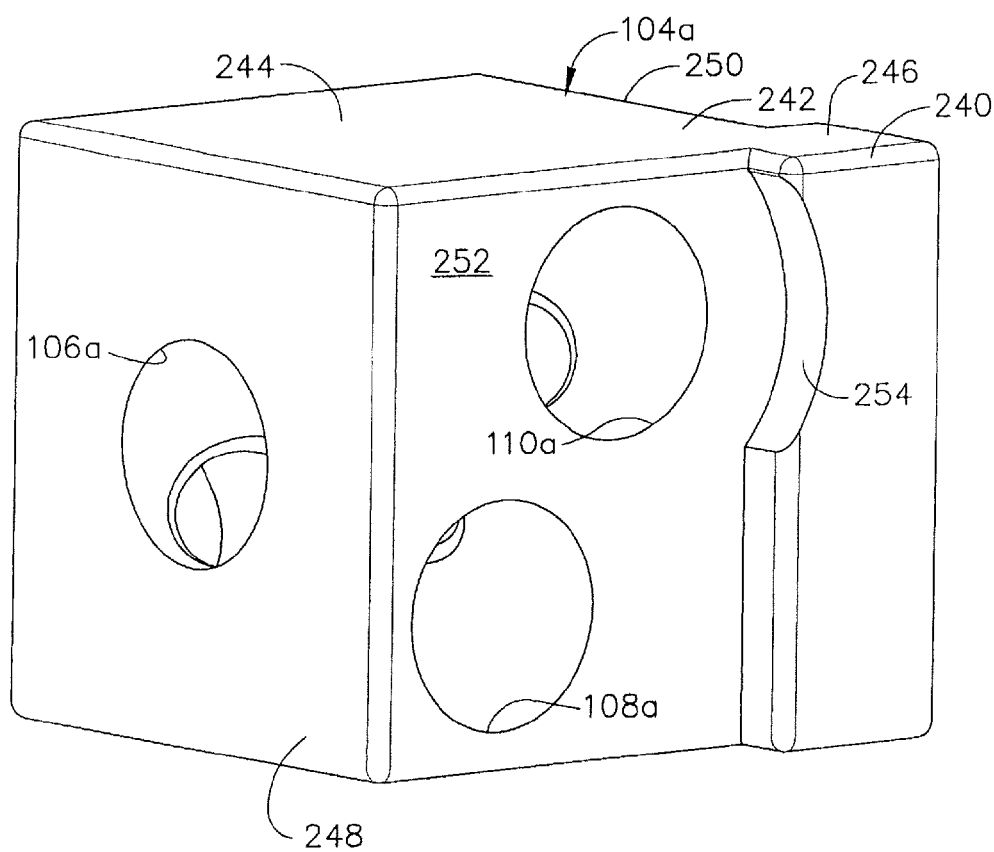
FIG. 10 is a perspective view of another guide cube for the biopsy system of FIG. 1 with a self-grounding feature.
Figure 11:
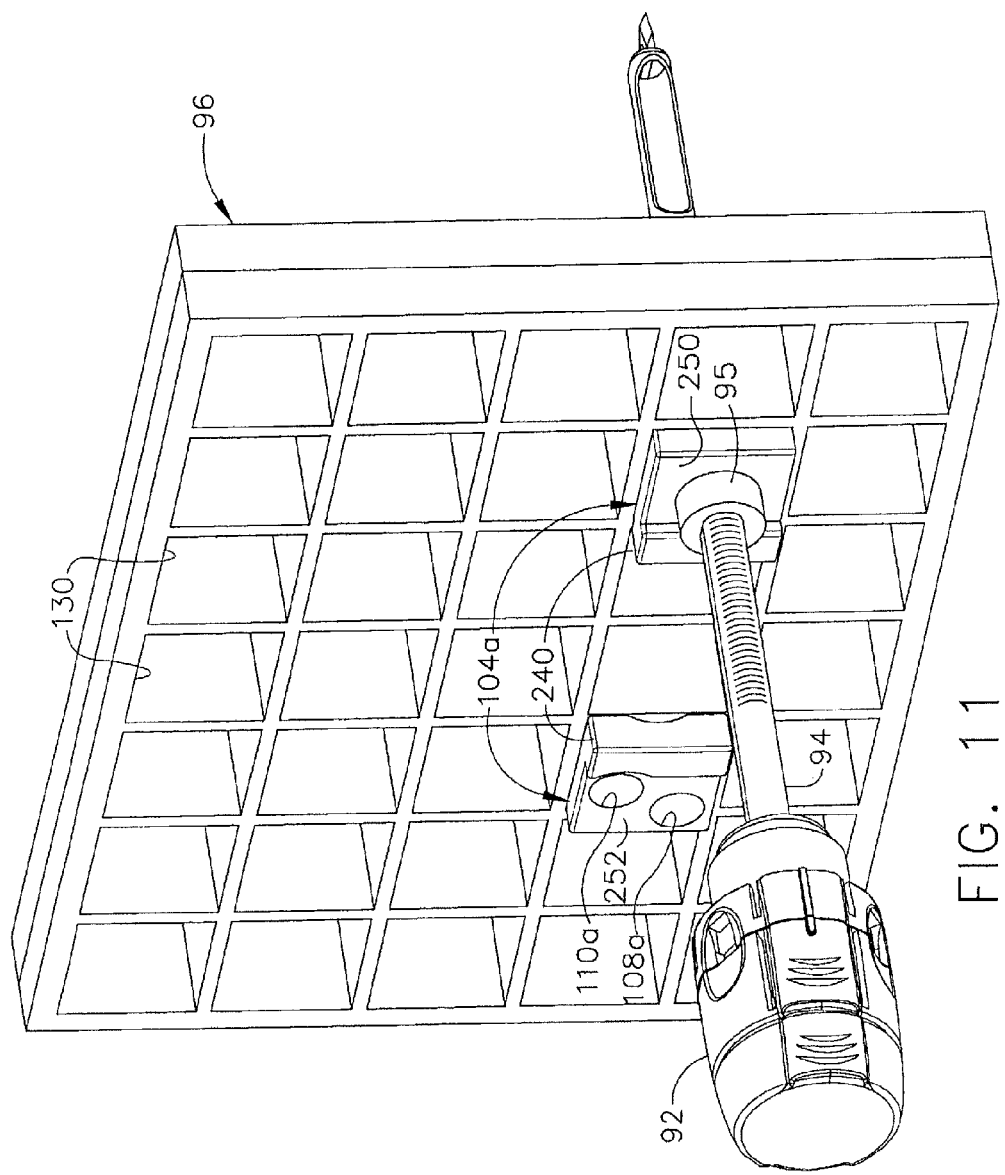
FIG. 11 is a perspective view of the obturator and cannula of FIG. 1 inserted into one of two guide cubes of FIG. 10 inserted into the grid plate of FIG. 1.

In FIG. 10, guide cube (104a) has self-grounding by means of added rectangular prism (240) which has a shared edge with cubic portion (242) of guide cube (104a). When viewed orthogonally to the shared cube edge, larger square face (244) of cubic portion (242) overlaps with smaller square face (246) of rectangular prism (240). As shown in FIG. 11, rectangular prism (240) allows proximal exposure of one of two adjacent faces (250, 252) of guide cube (104a) and then turning each to one of four quarter-turn rotational positions. In the illustrative version, first face (250) has central guide hole (106a) and second face (252) has corner guide hole (108a), and off-center guide hole (110a). Radial recess (254) is formed in rectangular prism (240) to allow grounding of depth stop device (95) against face (252) when off-center guide hole (110a) is used.

Figure 12:
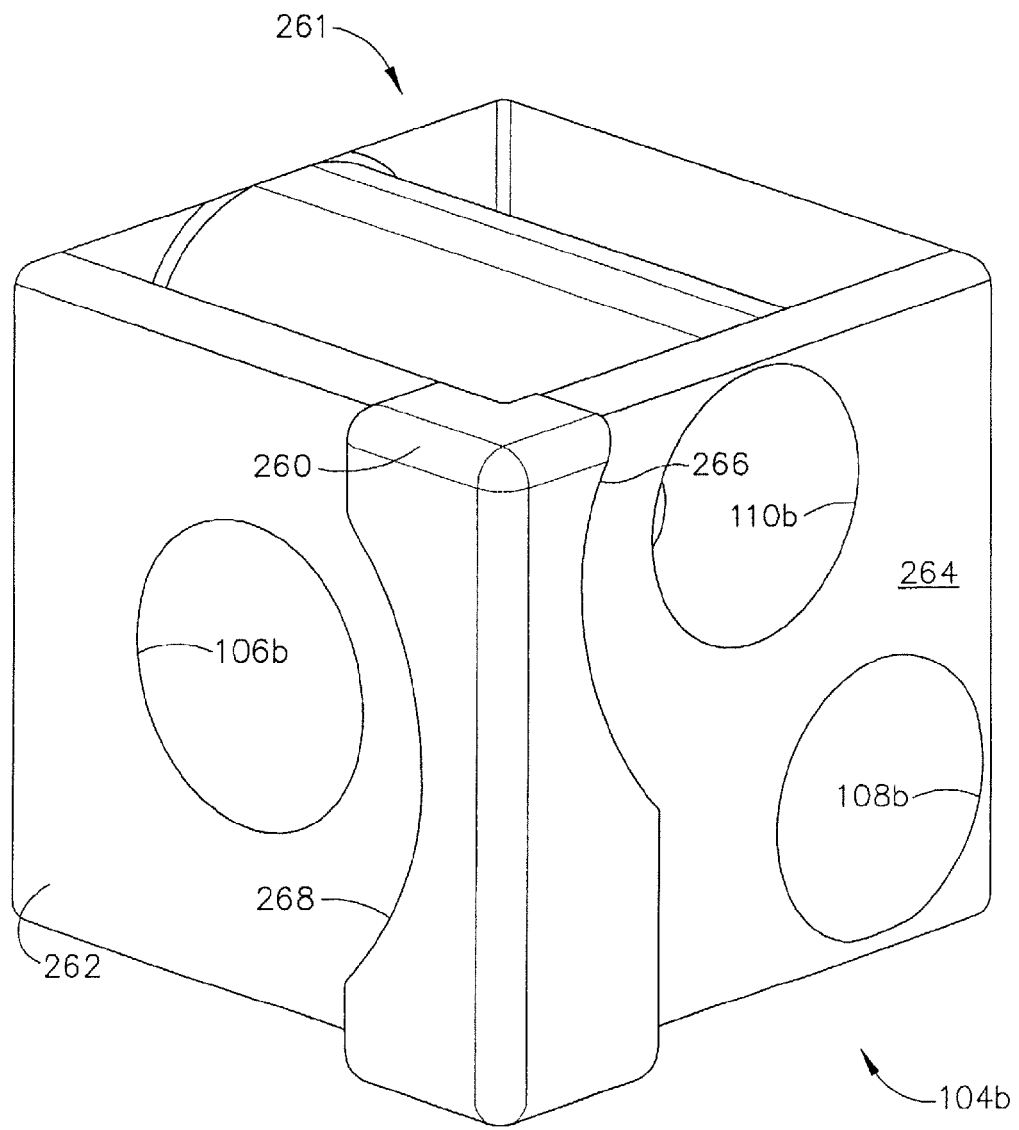
FIG. 12 is a perspective view of another exemplary guide cube having an open top and bottom with another self-grounding feature.

In FIG. 12, guide cube (104b) has self-grounding by means of added rectangular prism (260) that protrudes from two faces (262, 264) of guide cube (104b). Rectangular prism (260) allows proximal exposure of one of two adjacent faces (262, 264) of guide cube (104b) and then turning each to one of four quarter-turn rotational positions. In the illustrative version, first face (262) has central guide hole (106b) and second face (264) has corner guide hole (108b) and off-center guide hole (110b). First radial recess (266) is formed in rectangular prism (260) to allow grounding of depth stop device (95) against face (264) when off-center guide hole (110b) is used. Second radial recess (268) is formed in rectangular prism (260) to allow grounding of depth stop device (95) against face (262) when central guide hole (106b) is used. As discussed in greater detail below, guide cube (104b) may have open top (261) and/or an open bottom (not shown) defined by the faces of guide cube (104b) as depicted in the illustrated version.

Figure 13:
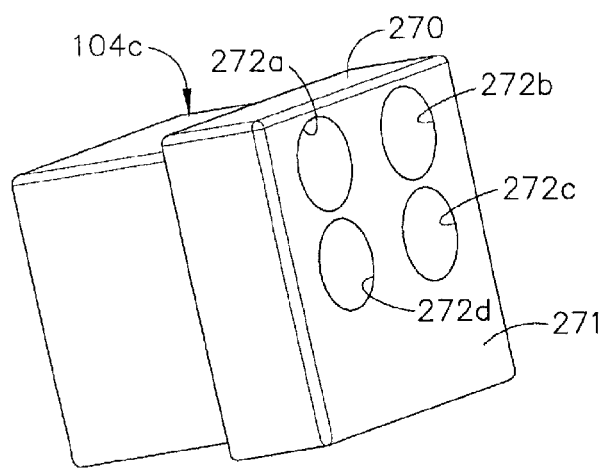
FIG. 13 is a rear perspective view of another exemplary guide cube with another self-grounding feature.
Figure 14:
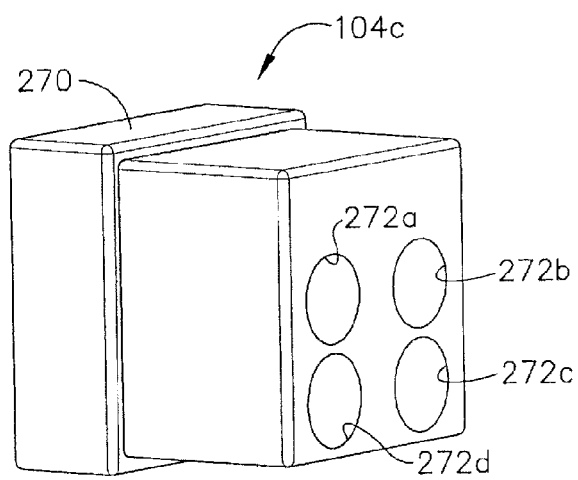
FIG. 14 is a front perspective view of the guide cube of FIG. 13.
Figure 15:
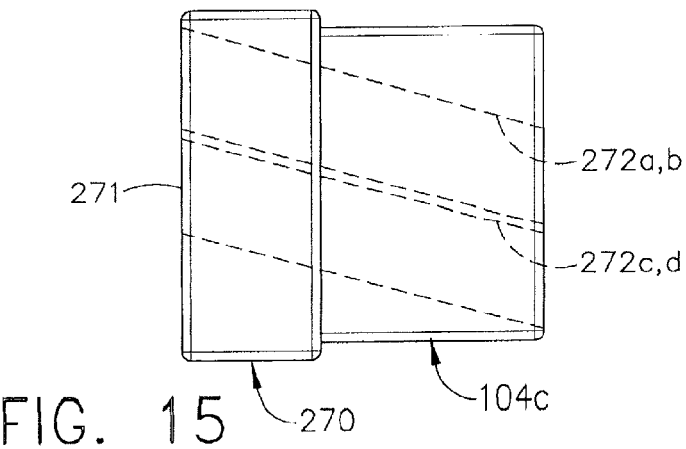
FIG. 15 is a right side view of the guide cube of FIG. 13 with angled, parallel guide holes depicted in phantom.
Figure 16:
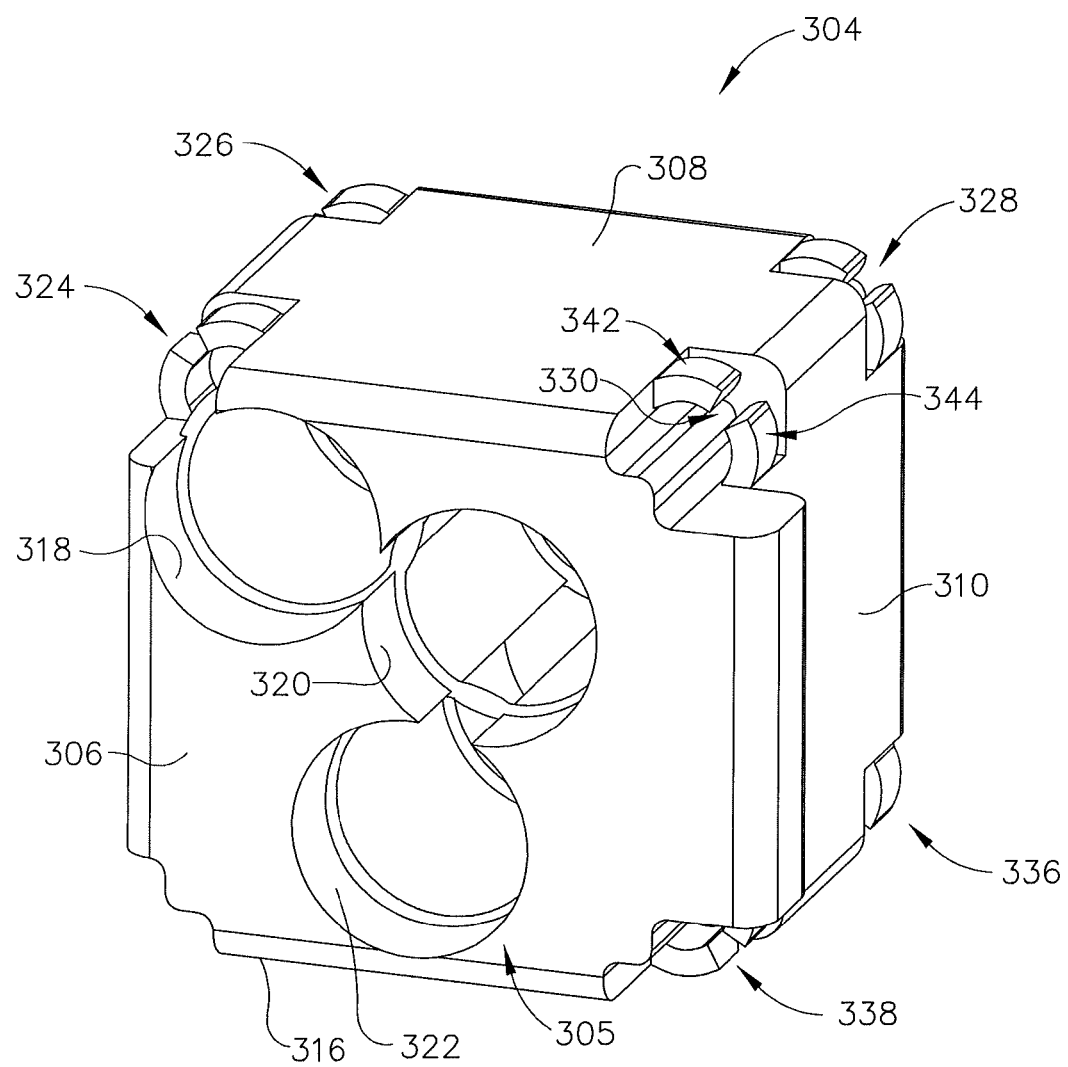
FIG. 16 is a front perspective view of another exemplary guide cube, with snap corners.
Figure 17:
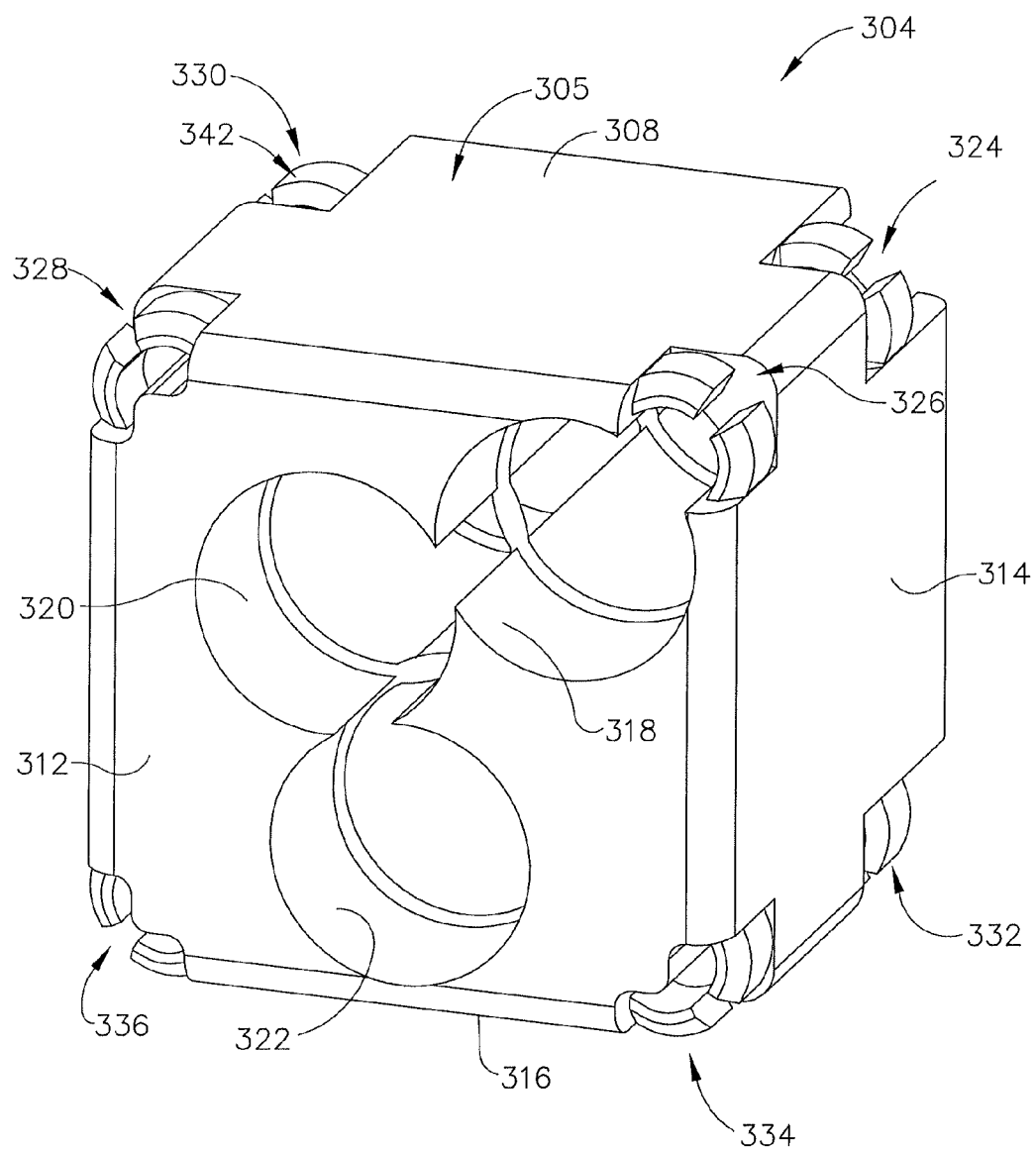
FIG. 17 is a rear perspective view of the guide cube of FIG. 16.

In FIGS. 13-15, guide cube (104c) has proximal enlarged hat portion (270) about proximal face (271) that grounds against selected square recess (130), such as in grid plate (96), and allows rotation about one axis to one of four quarter-turn positions. Four angled guide holes (272a, 272b, 272c, 272d) allow accessing not only an increased number of insertion points within selected square recess (130) but also a desired angle of penetration rather than being constrained to a perpendicular insertion. It will be appreciated based on the teachings herein that while angled guide holes may be used in some versions, orthogonal guide holes may be used instead of or in addition to angled guide holes in other versions.

C. Snap Corners

In some versions of guide devices, the guide device may include features that assist in securing the guide device within an aperture of a grid plate. Such features may be configured to secure the guide device from movement in a proximal direction, distal direction, lateral direction, or combinations of these or other directions. For instance, such features may substantially retain the guide device by providing restriction on or resistance to movement of the guide device relative to the grid plate (96) upon sufficient engagement between the guide device and grid plate (96). In some versions of guide devices, the guide devices may further include features that assist in securing an instrument, such as a biopsy device (14) or a portion of a biopsy device (14) (e.g., needle (90) of biopsy device (14), a combination of cannula (94) and obturator (92), etc.), within a selected guide hole or passageway of the guide device. In some versions, such features may substantially retain the instrument or portion of the instrument by providing resistance to movement of the instrument in a proximal direction, distal direction, rotational direction, lateral direction, or combinations of these or other directions. The paragraphs that follow will describe merely exemplary versions of guide devices or modifications to guide devices that may include some of these optional features, among features.

As shown in FIGS. 16-21, another exemplary guide cube (304) includes a body (305) that is generally defined by six faces (306, 308, 310, 312, 314, 316). Of course, body (305) may be defined by a greater or fewer number of faces as will be appreciated by one of ordinary skill in the art. By way of example only, body (305) may comprise just two faces positioned perpendicular to each other to form a bracket-like structure. Alternatively, body (305) may comprise three faces, where two faces are generally opposed in parallel fashion and the third face is positioned at right angles between the two opposed faces. Other suitable numbers and arrangements of faces will be apparent to those of ordinary skill in the art in view of the teachings herein. In the present example, guide cube (304) further comprises a corner guide hole (318), an off-center guide hole (320), and a bottom guide hole (322), each of which extend between opposite faces (306) and (312). As with other guide holes described herein, guide holes (318, 320, 322) provide passageways configured to permit insertion of an instrument (e.g., needle (90) of probe (91), obturator/cannula (92, 94), etc.) through body (305), such that a selected guide hole (318, 320, 322) may provide an insertion guide for the instrument at a selected position and orientation. For instance, guide cube (304) may be rotated about an axis passing through faces (306, 312) to provide selective positioning and orientation of guide holes (318, 320, 322). Other variations of guide cube (304) may provide other guide hole configurations (e.g., guide holes through more than just two faces, etc.), such that guide cube (304) may be rotatable about two or three axes to provide selective positioning and orientation of guide holes, as will be apparent to those of ordinary skill in the art in view of the teachings herein.

The faces (306, 308, 310, 312, 314, 316) of guide cube (304) further define eight corners (324, 326, 328, 330, 332, 334, 336, 338). Of course, it will be understood by one of ordinary skill in the art that guide cube (304) may comprise a greater or fewer number of corners that may depend on the number of faces comprising the guide cube body (305) or other factors. By way of example only, a body (305) comprising just two faces positioned perpendicular to each other to form a bracket-like structure may form only two corners at the juxtaposition of the two faces. Alternatively, a body (305) comprising three faces, where two faces are generally opposed in parallel fashion and the third face is positioned at right angles between the two opposed faces, may define four corners at the intersections of the perpendicular third face with the two generally opposed faces. Other suitable numbers and arrangements of cube corners will be apparent to those of ordinary skill in the art in view of the teachings herein. Because corners (324, 326, 328, 330, 332, 334, 336, 338) are identical in structure and function in the present example, the remainder of this application will refer only to corner (330) for ease of description, except where a distinction is necessary.

Figure 18:
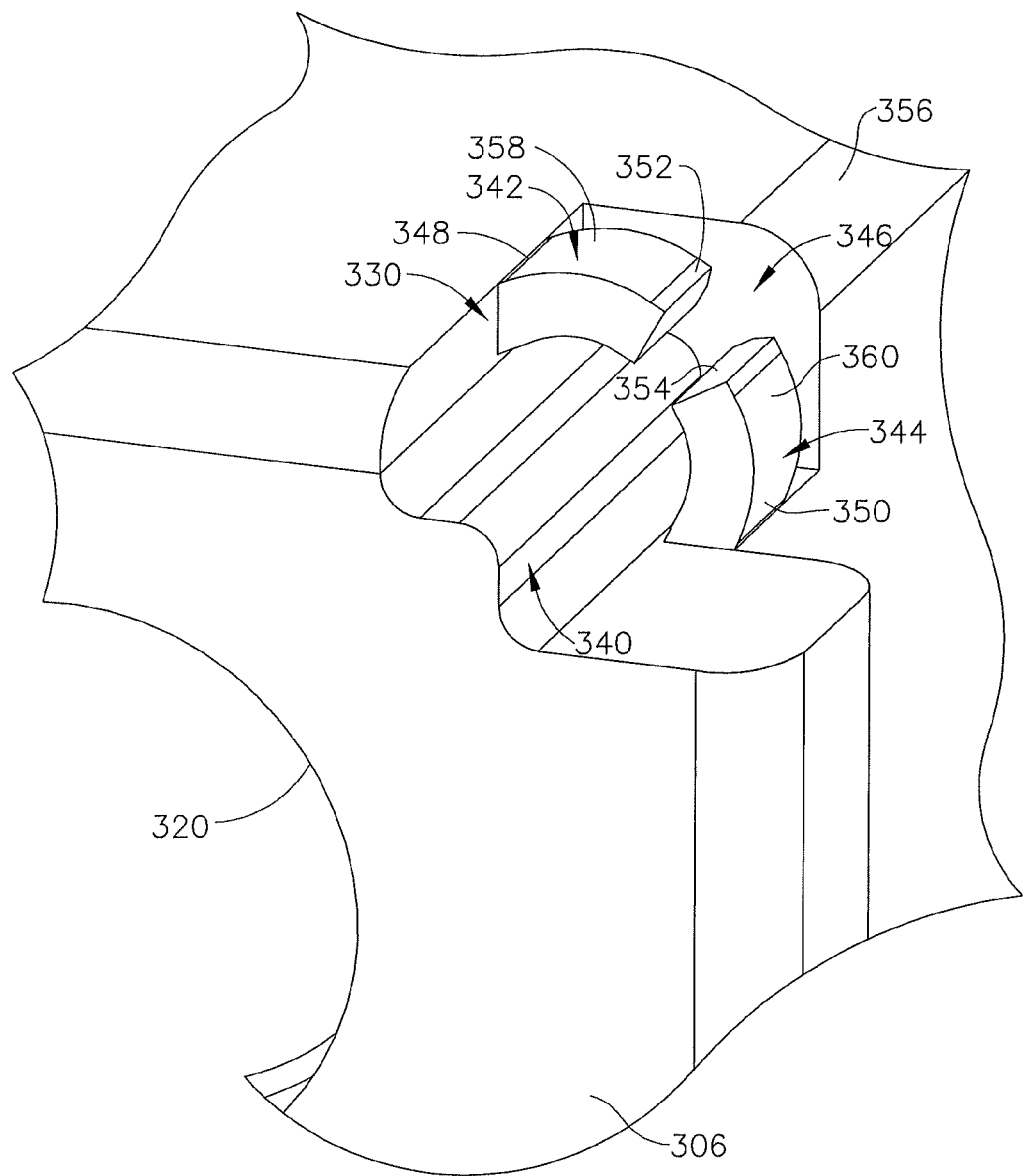
FIG. 18 is a partial front perspective view of an exemplary snap corner of the guide cube of FIG. 16.

As illustrated in FIG. 18, corner (330) comprises a cutout section (340) and two deflectable projections (342, 344) to securely and removably fit guide cube (304) within a grid plate (96). Although shown with two projections (342, 344), it will be understood that corner (330) may comprise any suitable number of projections to secure the cube (304) within a grid plate (96). By way of example only, corner (330) may have just one single projection, four projections, or any other suitable number of projections including zero projections. In the illustrative version, projections (342, 344) have a generally rectangular cross section having a first end (348, 350), a second end (352, 354), and a curved portion (358, 360) that extends between the first end (348, 350) and the second end (352, 354). The first ends (348, 350) engage the projections (342, 344) with the cube body (305) while the second ends (352, 354) extend towards each other forming a gap (346) in the space between the second ends (352, 354). Of course, projections (342, 344) may have any other suitable shape and should not be limited to a generally rectangular cross section. Projections (342, 344) may have a generally cylindrical cross section, for example.

Figure 19:
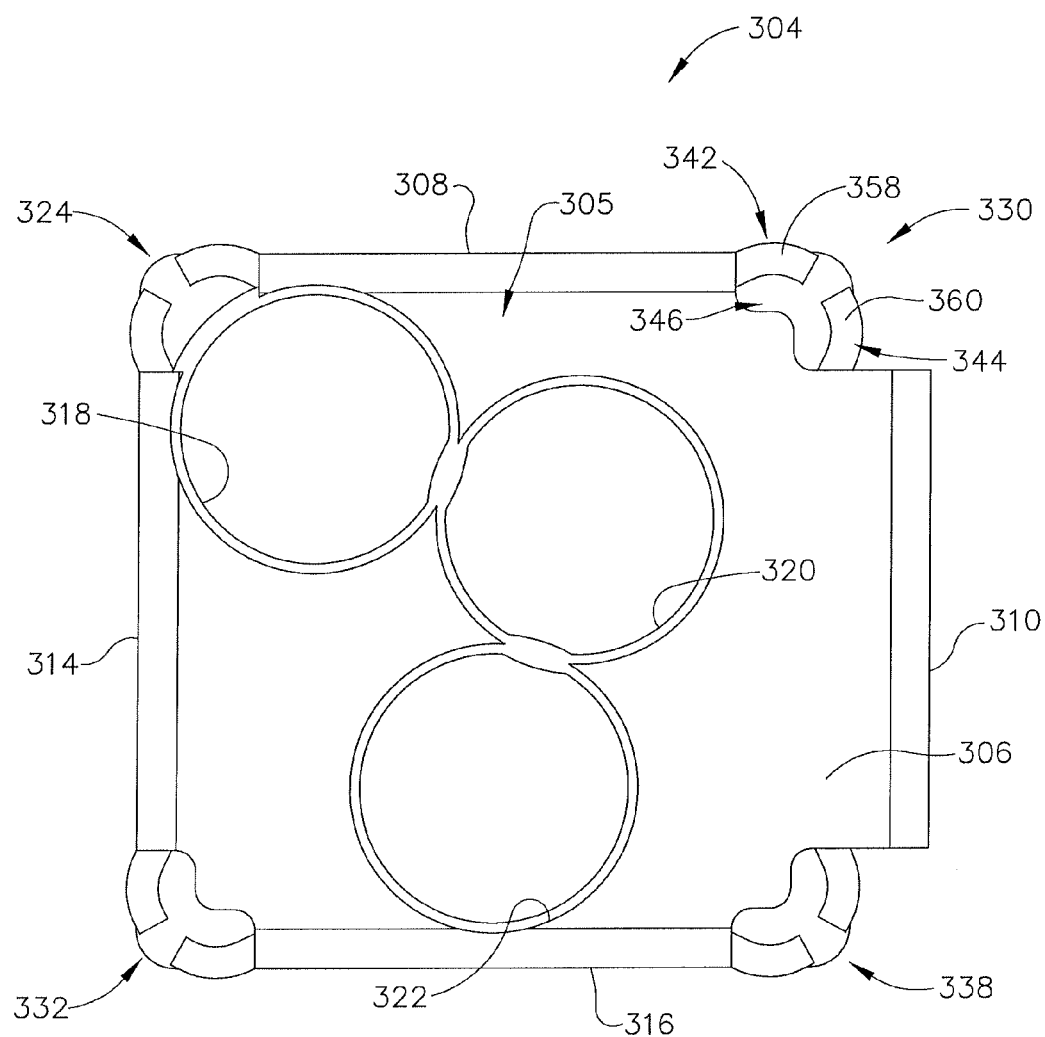
FIG. 19 is a front plan view of the guide cube of FIG. 16.

The illustrated projections (342, 344) are deflectable to secure a guide cube (304) into a recess (130) of a grid plate (96). As shown in FIG. 19, when not in contact with another object, projections (342, 344) extend outwardly away from cube body (305) in such a way that the curved portions (358, 360) of the projections (342, 344) are raised above and not quite flush with the faces (308, 310) of body (305). In other words, projections (342, 344) extend outwardly past the planes defined by faces (308, 310). As shown in FIGS. 16-21, the present example depicts projections positioned at the corners of guide cube (304) (for example, projections (342, 344) are positioned at corner (330)). One of ordinary skill in the art will understand, however, that the projections may be positioned at any other suitable location on guide cube body (305). For instance, projections (342, 344) may be positioned along edge (356) between corners (330, 328). As another merely illustrative example, projections (342, 344) may be positioned entirely outside the planes defined by faces (308, 310), instead of the projections (342, 344) intersecting the planes defined by faces (308, 310) as they do in the present example.

It should be understood that projections (342, 344) are resiliently biased to assume the outwardly projecting positions shown in FIG. 19. However, it should also be understood that the flexibility of projections (342, 344) as well as the gap (346) between projections (342, 344) permits projections (342, 344) to be bent inwardly toward each other. Thus, all of the projections (342, 344) of guide cube (304) may effectively define a first outer perimeter for guide cube (304) when projections (342, 344) are in their resiliently biased outward position; while all of the projections (342, 344) of guide cube (304) may effectively define a second outer perimeter for guide cube (304) when associated projections (342, 344) of each pair of projections (342, 344) are pushed toward each other, with the second outer perimeter being smaller than the first outer perimeter. As described in greater detail below, such a changeable effective outer perimeter may provide frictional assistance in retaining guide cube (304) in a grid plate (96). Furthermore, such a changeable effective outer perimeter may facilitate use of guide cube (304) in different grid plates (96) having differently sized recesses (130).

Figure 20:
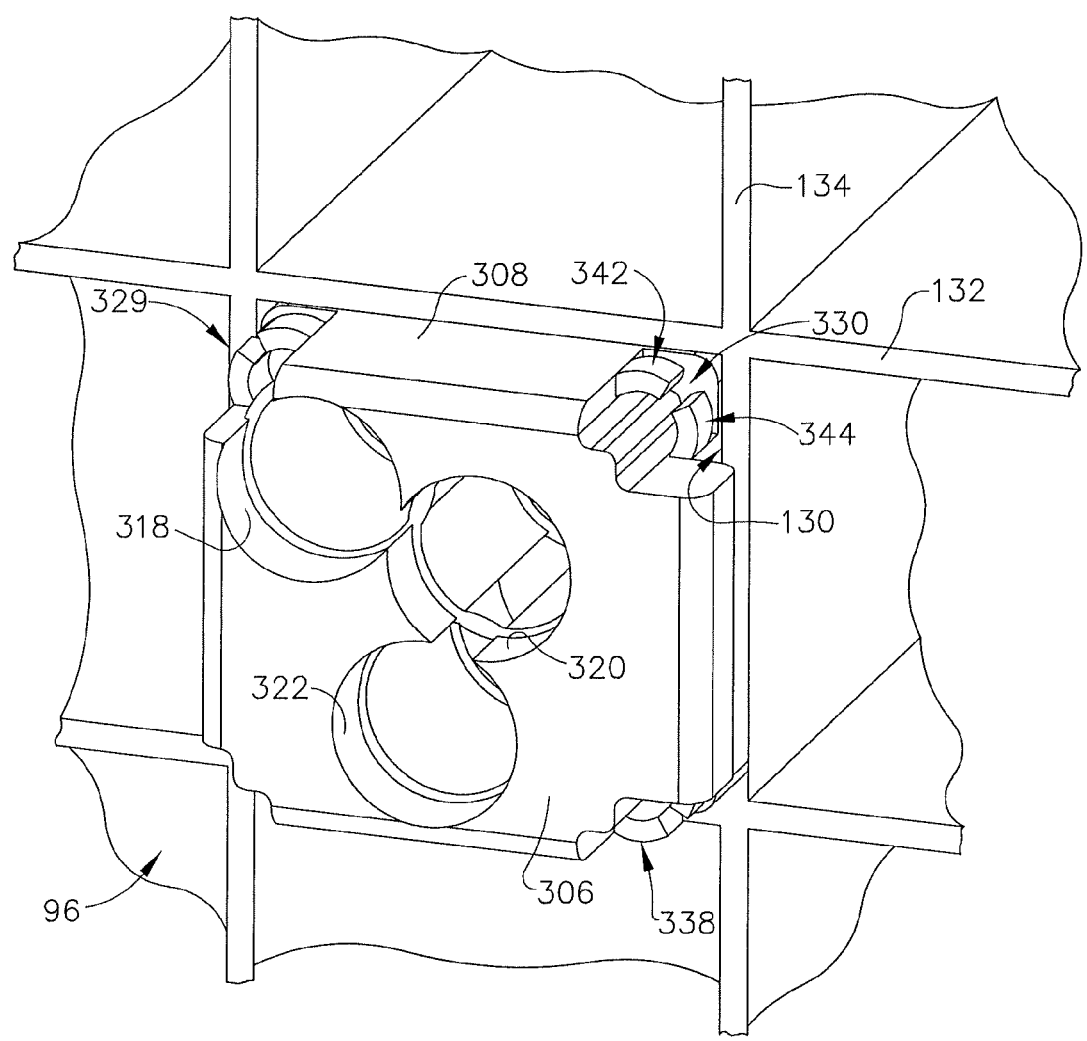
FIG. 20 is a perspective view of the guide cube of FIG. 16 partially inserted into a grid plate of a localization assembly.
Figure 21:
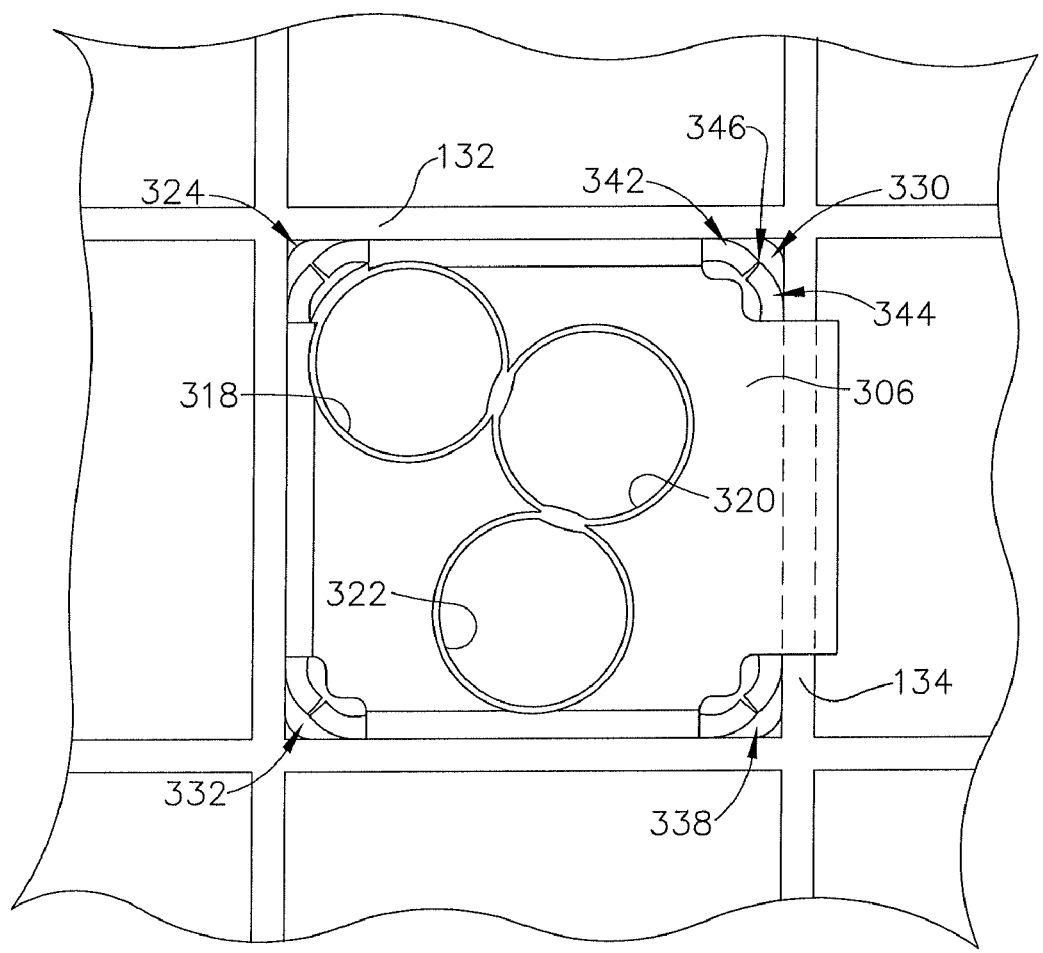
FIG. 21 is a front plan view of the guide cube of FIG. 16 inserted into a grid plate of a localization assembly, with snap corners of the guide cube engaged with the grid plate.
Figure 22:
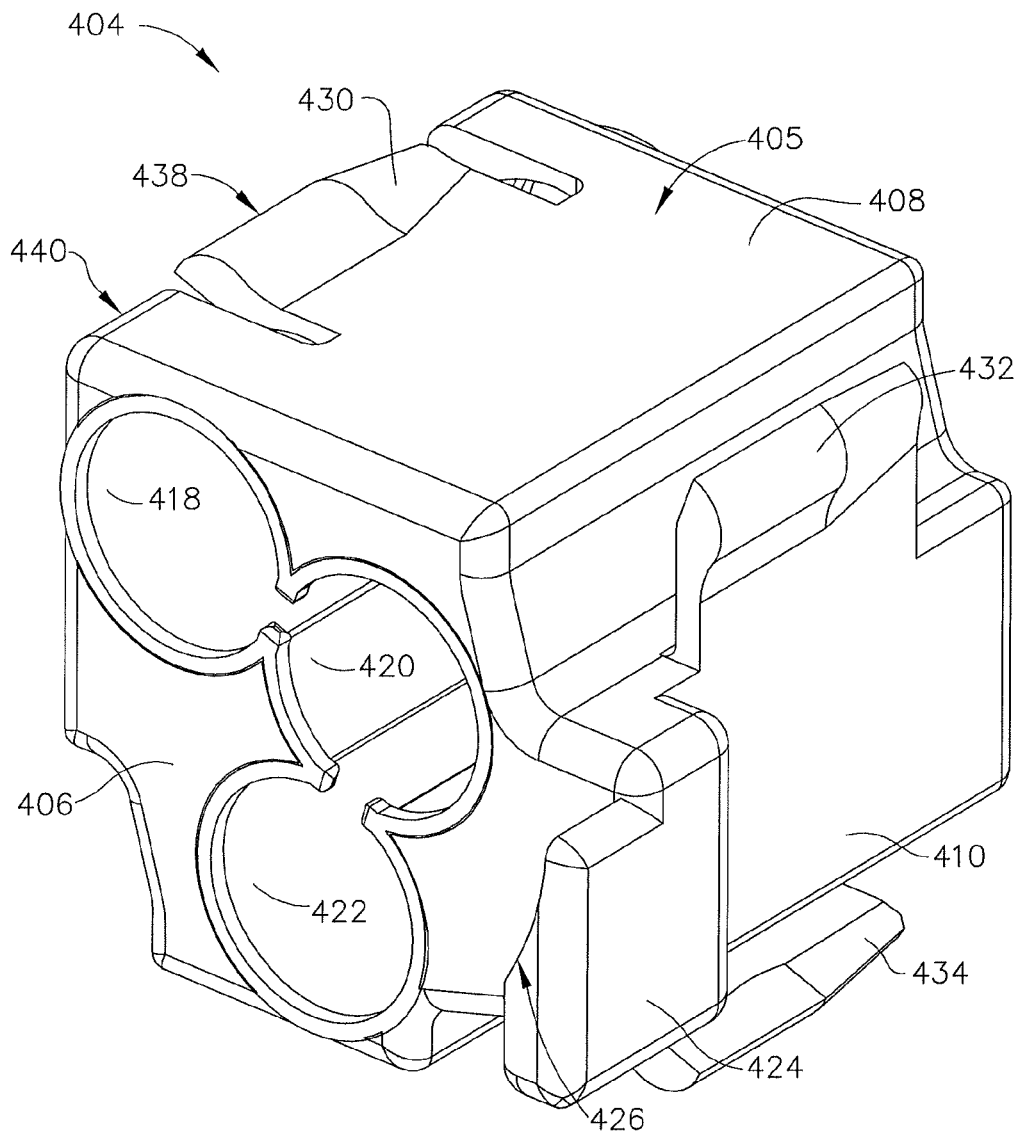
FIG. 22 is a front perspective view of another exemplary guide cube, with winged projections.
Figure 23:
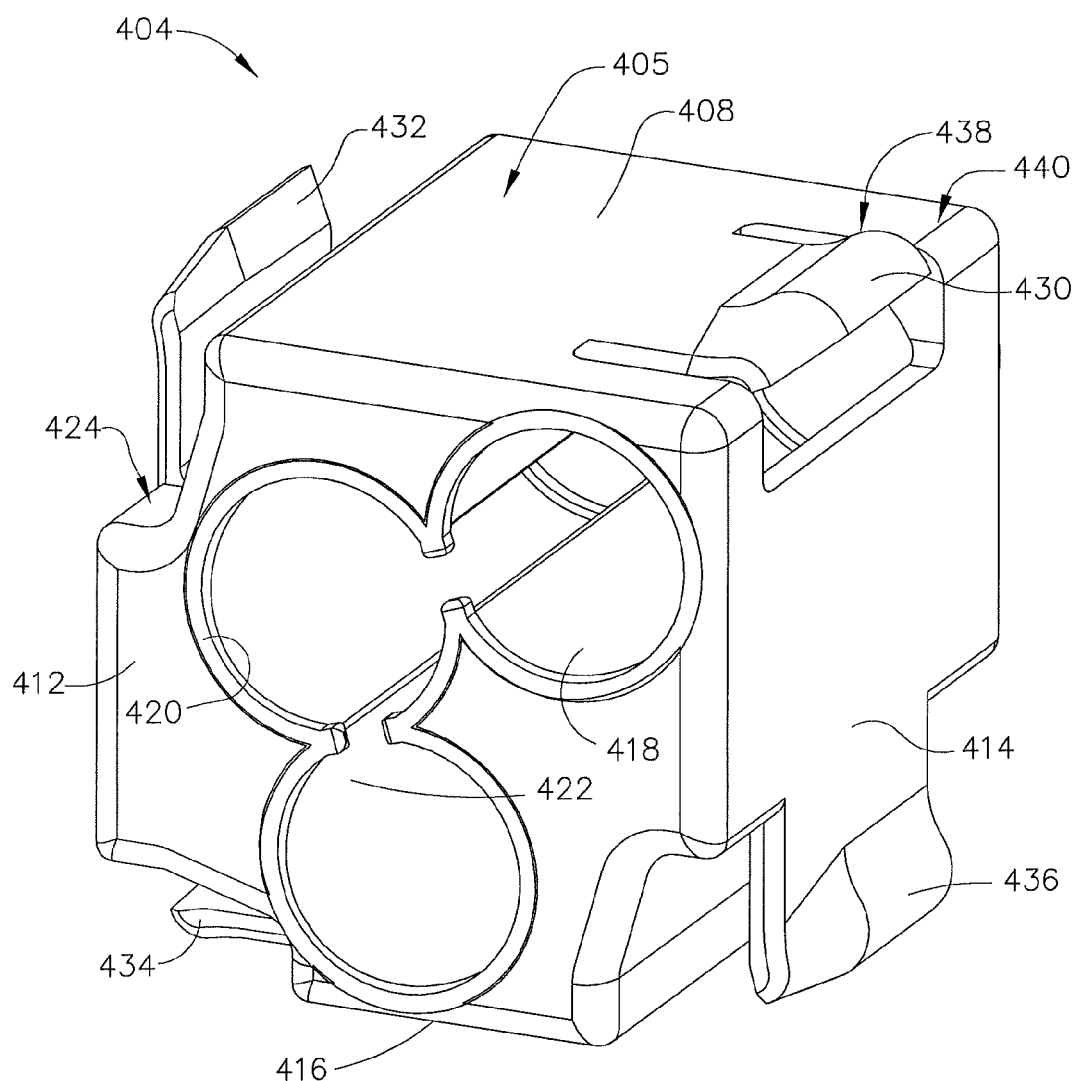
FIG. 23 is a rear perspective view of the guide cube of FIG. 22.

Referring to FIGS. 20-21, guide cube (304) may be inserted into a grid plate (96) to define the insertion point and/or insertion angle of an instrument (e.g., needle (90) of probe (91), obturator/cannula (92, 94), etc.) used to perform a biopsy. For example, guide cube (304) may be inserted on the medial side (i.e., side facing the breast tissue) of grid plate (96). Alternatively, guide cube (304) may be inserted on the lateral side of grid plate (96). Guide cube (304) fits into a square recess (130) of grid plate (96) by deflection of the projections positioned at the corners (324, 326, 328, 330, 332, 334, 336, 338) of the cube body (305). For example, projection (342) may be deflected toward projection (344) by contact with the horizontal bar (132) of grid plate (96). Likewise, projection (344) may be deflected toward projection (342) by contact with the vertical bar (134) of grid plate (96). The deflection of projection (342), projection (344), or both may cause the second ends (352, 354) of projections (342, 344) to near each other in such a way that the gap (346) between them grows smaller. Once cube (304) is in position within grid plate (96), the surface friction existing as a result of the contact between the deflected projections (342, 344) and grid plate bars (132, 134), as well as the resilient outward bias of projections (342, 344), secures the cube (304) in place within the recess (130) by providing some resistance to proximal, distal, or lateral movement or combinations of thereof of the cube (304) relative to grid plate (96).

As shown in FIGS. 22-25, another exemplary guide cube (404) includes a body (405) that is generally defined by six faces (406, 408, 410, 412, 414, 416). Of course, body (405) may be defined by a greater or fewer number of faces as will be appreciated by one of ordinary skill in the art. By way of example only, body (405) may comprise just two faces positioned perpendicular to each other to form a bracket-like structure. Alternatively, body (405) may comprise three faces, where two faces are generally opposed in parallel fashion and the third face is positioned at right angles between the two opposed faces. Other suitable numbers and arrangements of faces will be apparent to those of ordinary skill in the art in view of the teachings herein. In the present example, guide cube (404) further comprises a corner guide hole (418), an off-center guide hole (420), and a bottom guide hole (422), each of which extend between opposite faces (406) and (412). As with other guide holes described herein, guide holes (418, 420, 422) provide passageways configured to permit insertion of an instrument (e.g., needle (90) of probe (91), obturator/cannula (92, 94), etc.) through body (405), such that a selected guide hole (418, 420, 422) may provide an insertion guide for the instrument at a selected position and orientation.

Figure 24:
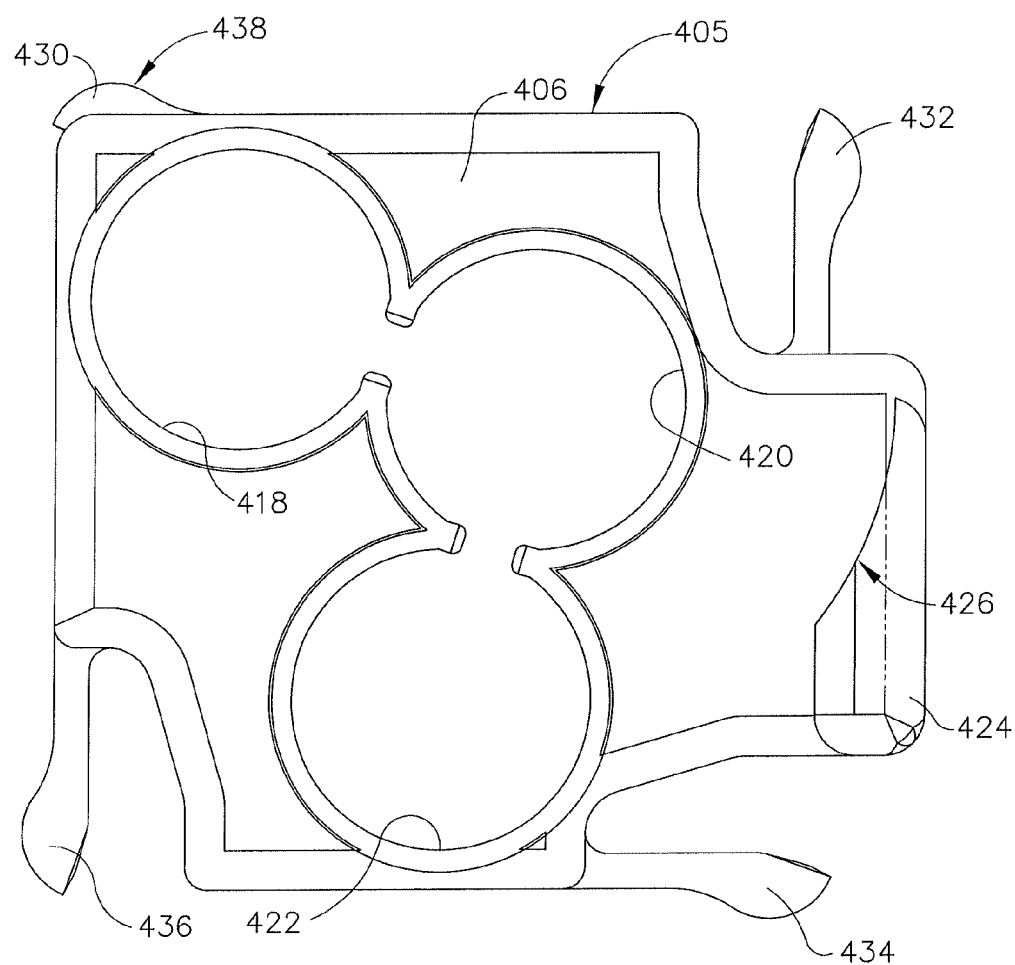
FIG. 24 is a front plan view of the guide cube of FIG. 22.
Figure 25:
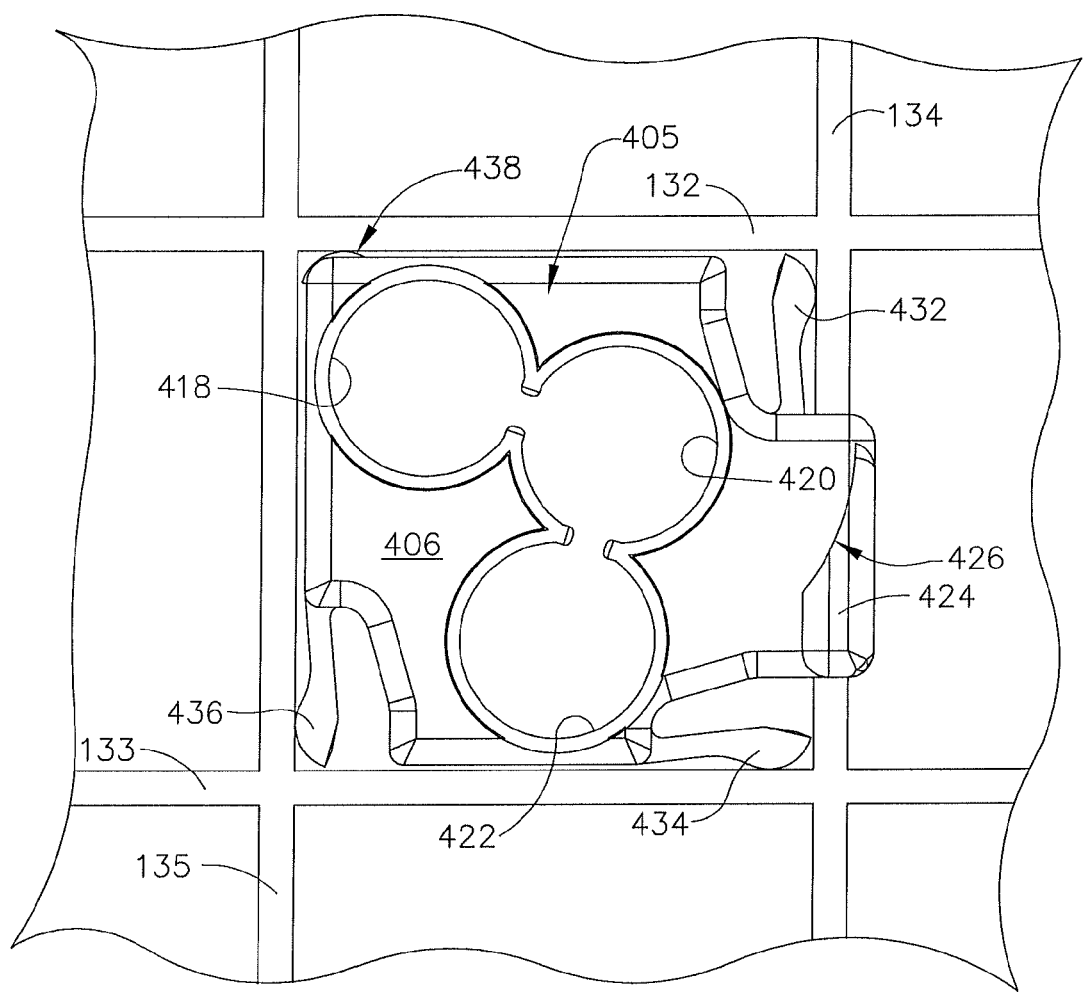
FIG. 25 is a front plan view of the guide cube of FIG. 22 inserted into a grid plate of a localization assembly, with winged projections of the guide cube engaged with the grid plate.

Guide cube (404) may also comprise a self-grounding means such as the exemplary rectangular prism (424) shown in FIGS. 22-25. Prism (424) may restrict the depth to which guide cube (404) may be inserted in grid plate (96) by grounding against one or more bars (132, 134) of grid plate (96). In the present example, prism (424) protrudes from faces (406, 410) and has a shared edge with cubic body (405). As shown in FIG. 25, such a prism (424) allows for proximal exposure of face (406) of cube (404) and then turning cube (404) (e.g., about the axis passing through faces (406, 412)) to a selected one of four quarter-turn rotational positions. Other variations of guide cube (404) may provide other guide hole configurations (e.g., guide holes through more than just two faces, etc.), such that guide cube (404) may be rotatable about two or three axes to provide selective positioning and orientation of guide holes, as will be apparent to those of ordinary skill in the art in view of the teachings herein. In addition, prism (424) may comprise a radial recess (426) to allow grounding of a depth stop device (95) against face (406) when off-center guide hole (420) is used. Of course, although the illustrated version depicts prism (424) as extending from faces (406, 410), it should be understood that prism (424) may be positioned in any other suitable location on cube body (405). By way of example only, prism may protrude from faces (406, 414) or faces (410, 412) or any other faces on cube (405). Furthermore, the shape of prism (424) need not be limited to a rectangular prism. One of ordinary skill in the art will understand that prisms of other shapes and configuration, such as cylindrical, are included within the scope of this application.

As illustrated in FIGS. 22-25, faces (408, 410, 414, 416) in the present example comprise winged projections (430, 432, 434, 436) to securely and removably fit guide cube (404) within a grid plate (96). Although shown with four winged projections (430, 432, 434, 436), cube (404) may comprise any suitable number of winged projections as will be recognized by one of ordinary skill in the art. For example, cube (404) may comprise a single winged projection, two winged projections, or six winged projections. Likewise, although the present example shows one winged projection (430, 432, 434, 436) per face (408, 410, 414, 416), the number of winged projections per cube face may be variable. By way of example only, face (408) may comprise no winged projections, two winged projections, or any suitable number of winged projections. Because winged projections (430, 432, 434, 436) are identical in structure and function in the present example, the remainder of this application will refer only to winged projection (430) for ease of description, except where a distinction is necessary.

As shown in FIGS. 22-25, winged projection (430) extends from face (408) and has a generally rectangular planar shape with slight curvature (438). Of course, it should be understood that winged projection (430) may have any other suitable shape and need not be limited to a generally rectangular shape. By way of example only, winged projection (430) may have a generally circular or ovular shape. In the illustrated version, winged projection (430) is positioned along an edge (440) of face (408) such that the projection (430) may be considered a part of the edge (440). As will be understood by one of ordinary skill in the art, however, winged projection (430) may be located in any suitable position along face (408). For example, winged projection (430) may positioned adjacent to edge (440), adjacent to any other edge comprising face (408), or in the interior of face (440).

In addition, the illustrated winged projection (430) is deflectable to secure a guide cube (404) into a recess (130) of a grid plate (96). As shown in FIG. 24, when not in contact with another object, winged projection (430) extends outwardly away from cube body (405) in such a way that the curved portions (438) is raised above and not quite flush with face (408). In other words, projection (430) extends outwardly past the plate defined by face (408). It should be understood that projection (430) is resiliently biased to assume the outwardly projecting positions shown in FIG. 24. However, it should also be understood that the flexibility of projection (430) as well as the gap between projection (430) and the body of guide cube (404) permits projection (430) to be bent inwardly toward the body of guide cube (404). Thus, all of the projections (432, 434, 436, 438) of guide cube (404) may effectively define a first outer perimeter for guide cube (404) when projections (432, 434, 436, 438) are in their resiliently biased outward position; while all of the projections (432, 434, 436, 438) of guide cube (404) may effectively define a second outer perimeter for guide cube (404) when projections (432, 434, 436, 438) are pushed inwardly toward the body of guide cube (404), with the second outer perimeter being smaller than the first outer perimeter. As described in greater detail below, such a changeable effective outer perimeter may provide frictional assistance in retaining guide cube (404) in a grid plate (96). Furthermore, such a changeable effective outer perimeter may facilitate use of guide cube (404) in different grid plates (96) having differently sized recesses (130).

Referring to FIG. 25, guide cube (404) may be inserted into a grid plate (96) to define the insertion point and/or insertion angle of an instrument (e.g., needle (90) of probe (91), obturator/cannula (92, 94), etc.) used to perform a biopsy. For example, guide cube (404) may be inserted on the medial side (i.e., side facing the breast tissue) of grid plate (96). Alternatively, guide cube (304) may be inserted on the lateral side of grid plate (96). Guide cube (404) fits into a square recess (130) of grid plate (96) by deflection of the winged projections (430, 432, 434, 436) extending from faces (408, 410, 414, 416) of the cube body (405). For example, winged projection (430) may be deflected inwardly by contact with the horizontal bar (132) of grid plate (96). The inward deflection of winged projection (430) may cause it to become substantially flush with face (408) in some settings. Once cube (404) is in position within grid plate (96), the surface friction existing as a result of the contact between the deflected projections (430, 432, 434, 436) and grid plate bars (132, 133, 134, 135), as well as the resilient outward bias of projections (430, 432, 434, 436), secures the cube (404) in place within the recess (130) by providing some resistance to proximal, distal, or lateral movement or combinations of thereof of the cube (404) relative to grid plate (96).

It should be understood that the above-described guide cubes (304, 404) are merely exemplary. Any other suitable type of guide cube (304, 404) and associated components may be used. By way of example only, guide cubes (304, 404) may include any suitable arrangement of guide holes and need not be limited to only including a corner hole (318, 418), an off-center hole (320, 420), and a bottom hole (322, 422) as in the illustrated versions. In some versions, guide cube (304, 404) may include only a central guide hole. In some other versions, guide cube (304, 404) may include one or more guide holes on one or more cube faces, and guide cube (304, 404) may be rotatable to provide for alternate guide hole orientations. In still other versions, guide cube (304, 404) may comprise slits or similar features instead of guide holes (318, 320, 322, 418, 420, 422), to provide a passageway between opposing faces. It is also noted that guide cube (304, 404) may be formed of a substantially rigid material, of an elastomeric material, and/or of any other suitable material, including combinations of materials.

In some versions, guide holes (318, 320, 322, 418, 420, 422) may each include one or more elastomeric retainers (not shown). Such retainers may be positioned within guide holes (318, 320, 322, 418, 420, 422) and/or at the entry of guide holes (318, 320, 322, 418, 420, 422) (e.g., at face (306, 406) or face (312, 412), etc.). By way of example only, such elastomeric retainers may comprise an o-ring, a duckbill seal, or some other structure. Such elastomeric retainers may be configured to substantially seal off breast tissue from the instrument (e.g., needle (90) of probe (91), obturator/cannula (92, 94), etc.) that is inserted into the guide hole (318, 320, 322, 418, 420, 422) to maintain a sterile environment. In addition or in the alternative, such retainers may be operatively configured to assist in securing an instrument such as a biopsy device (14) or a portion of a biopsy device (14) (e.g., needle (90) of biopsy device (14), a combination of cannula (94) and obturator (92), etc.) within a selected guide hole (318, 320, 322, 418, 420, 422). In particular, retainers may be configured such that the opening defined by the combination of the retainer and its corresponding guide hole (318, 320, 322, 418, 420, 422) is smaller in diameter than the diameter of the instrument, e.g. cannula (94), that is to be inserted in a selected guide hole (318, 320, 322, 418, 420, 422). When cannula (94) is inserted in a selected guide hole (318, 320, 322, 418, 420, 422), the retainer may compress, deform, and/or fold over to provide for a secure fit. In other words, a retainer permits distal insertion of cannula (94) or needle (90), etc., through a selected guide hole (318, 320, 322, 418, 420, 422), while friction between the inserted instrument and the elastomeric material of retainer provides some resistance to proximal movement of the inserted instrument relative to guide hole (318, 320, 322, 418, 420, 422). In some versions, the securing force provided by the retainer is such that the compressed tissue of a patient will not displace cannula (94) proximally from guide hole (318, 320, 322, 418, 420, 422) during a biopsy procedure. Retainers may thus provide resistance against proximal withdrawal of the instrument.

It should also be understood that each guide hole (318, 320, 322, 418, 420, 422) may have more than one associated retainer. For instance, each guide hole (318, 320, 322, 418, 420, 422) may have two or more retainers that are axially staggered along the length of guide hole (318, 320, 322, 418, 420, 422).

While retainers are described as a feature providing resistance to withdrawal of an inserted instrument from guide cube (304, 404) while not significantly providing resistance to insertion of the instrument into guide cube (304, 404), it should be understood that a variety of other components or features may be used to provide similar results. Similarly, it should be understood that retainers may be modified or varied in numerous ways, if not be omitted altogether. Various ways in which retainers may be modified, varied, substituted, or supplemented will be apparent to those of ordinary skill in the art in view of the teachings herein.

Based on the teachings herein, those of ordinary skill in the art will appreciate that several elastomeric materials may be suitable for use with guide cube (304, 404), including but not limited to the use of elastomeric materials to form retainers. Such elastomeric materials may be used to form at least part of the body (305, 405) of guide cube (304, 404), to enhance friction at the projections (342, 344) of cube (304), to enhance friction at the winged projections (430, 432, 434, 436) of cube (404), and/or to form other components of guide cube (304, 404). By way of example only, suitable elastomeric materials may include thermosetting plastics that may require vulcanization, thermoplastic elastomers (e.g. Santoprene™ among others), natural rubber, synthetic rubbers (e.g. ethylene propylene diene M-class—EPDM—among others), and other polymers having suitable elastic properties. Other suitable elastomeric materials will be apparent to those of ordinary skill in the art in view of the teachings herein. Similarly, other suitable properties that materials forming various parts of guide cube (304, 404) may have will be apparent to those of ordinary skill in the art in view of the teachings herein.

Creating a guide cube (304, 404) having elastomeric retainers and/or other elastomeric components/features may be accomplished in a variety of ways. For example, in creating a guide cube such as a guide cube (304, 404) that has elastomeric retainers, in some versions a multi-shot molding process may be used where the body of guide cube (304, 404) may be molded from a first material, e.g. a non-elastomeric material such as hard plastic, and the elastomeric retainers may be molded from a second material, e.g. an elastic material as described herein or otherwise. In some other versions, elastomeric retainers may be molded or extruded separate from the body of guide cube (304, 404) and then coupled with the body of guide cube (304, 404) by mechanical fastening, chemical adhesive, or other suitable bonding or coupling techniques. For instance, guide cube (304, 404) may be molded of substantially hard plastic material, with slots or recesses formed in guide holes (318, 320, 322, 418, 420, 422) to receive annular elastomeric retainers. Retainers, being separately formed of an elastomeric material, may then be inserted and secured in these slots or recesses. In some other versions, guide cube (304, 404) with retainers may be molded as a single unitary piece having a uniform composition of elastomeric material. Various other suitable ways in which elastomeric retainers and/or other elastomeric components/features may be incorporated into guide cube (304, 404) before, during, or after manufacturing processes will be apparent to those of ordinary skill in the art in view of the teachings herein.

It should be understood that any feature(s) and/or operability described herein with respect to one particular guide cube or device (104, 104a, 104b, 104c, 304, 404) may be incorporated into any other guide cube or device (104, 104a, 104b, 104c, 304, 404) described herein. By way of example only, any of guide cubes or devices (104, 104a, 104b, 104c) may be modified to include projections (342, 344) (or variations thereof) similar to guide cube (304), winged projections (430, 432, 434, 436) similar to guide cube (404), and/or retainers similar to guide cubes (304, 404). Similarly, any guide cube or device (104, 104a, 104b, 104c, 304, 404) described herein may be used in accordance with the exemplary uses taught herein with respect to one particular guide cube or device (104, 104a, 104b, 104c, 304, 404) described herein. Therefore, none of the teachings herein should be understood as applying to only one particular version or embodiment of guide cube or device (104, 104a, 104b, 104c, 304, 404) described herein. Every teaching herein is contemplated as being interchangeable among versions and embodiments, such that every teaching herein may be applied to any guide cube or device (104, 104a, 104b, 104c, 304, 404) described herein. Various ways in which the teachings herein may be interchanged among various versions and embodiments will be apparent to those of ordinary skill in the art in view of the teachings herein.

As noted above, any guide cube or device (104, 104a, 104b, 104c, 304, 404) described herein may be used in a procedure that includes the use of PEM imaging, BSGI imaging, or any other suitable type of imaging. By way of example only, a guide cube or device (104, 104a, 104b, 104c, 304, 404) may be used with a grid plate (96) that is configured for use in an MRI setting, a grid plate for use in a nuclear/molecular imaging setting, or with some other type of cube holder (e.g., "guide holder") used in nuclear/molecular imaging or other type of imaging. For instance, a suitable alternative cube holder or "guide holder" may include fewer openings (e.g., one to four) that are configured to receive a guide cube or device (104, 104a, 104b, 104c, 304, 404) as compared to the number of recesses (130) in grid plate (96). Furthermore, a guide cube or device (104, 104*a*, 104*b*, 104*c*, 304, 404) may be used with a biopsy device (14) in conjunction with a full targeting set or with just a biopsy device (14) (e.g., in settings where a radioisotope can be communicated through the biopsy device (14)). It should also be understood that a guide cube or device (104, 104*a*, 104*b*, 104*c*, 304, 404) may be used just with a radioisotope, without necessarily involving any biopsy device (14). For instance, a radioisotope may be provided on or through an implement that has a sharp tip, and the implement may be inserted through the guide cube or device (104, 104*a*, 104*b*, 104*c*, 304, 404). Still other various settings and combinations in which a guide cube or device (104, 104*a*, 104*b*, 104*c*, 304, 404) may be used will be apparent to those of ordinary skill in the art in view of the teachings herein.

While several guide cubes have been discussed in detail above, it should be understood that the components, features, configurations, and methods of using the guide cubes discussed are not limited to the contexts provided above. In particular, components, features, configurations, and methods of use described in the context of one of the guide cubes may be incorporated into any of the other guide cubes. One merely exemplary additional feature that may be provided in any of the guide cubes described herein is one or more ridges on one or more external faces of the cube. Such ridges may be substantially rigid, elastomeric, or have any other suitable properties. Such ridges may provide a more secure fit between a cube and grid (e.g., reducing the likelihood that that the guide cube will undesirably fall out of the grid plate), may permit a single cube to be inserted in different grids having differently sized openings, and/or may provide other results. Still other additional and alternative suitable components, features, configurations, and methods of using the guide cubes will be apparent to those of ordinary skill in the art in view of the teachings herein.

Versions of the present invention have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A guide device for guiding a medical instrument relative to a patient, the guide device being usable with a first plate and a second plate, wherein the first plate has a plurality of apertures defined by a plurality of intersecting walls, wherein the second plate and the first plate are adjustable to secure a portion of the patient, wherein the guide device is configured to be coupled with a selected one of the apertures of the first plate, the guide device comprising:
   a. a body having a generally proximal side, a generally distal side, and a first generally lateral side extending between the generally proximal side and the generally distal side;
   b. at least one passageway, wherein the at least one passageway extends from the generally proximal side of the body to the generally distal side of the body, wherein the at least one passageway is configured to receive at least a portion of the medical instrument; and
   c. a first projection extending outwardly from the body, wherein the first projection is resiliently biased to extend outwardly, wherein the first projection is operable to be deflected inwardly through contact with a first wall defining the selected one of the apertures in the first plate to securably and removably fit the guide device within the first plate.

2. The guide device of claim 1, wherein the body further comprises a first corner, wherein the first projection is located at the first corner.

3. The guide device of claim 2, wherein the first projection comprises a first end, a second end, and a curved portion, and wherein the first end of the first projection engages with the first corner of the body and the curved portion of the first projection extends between the first and second ends of the first projection.

4. The guide device of claim 3, further comprising a second projection extending from the body, wherein the second projection is operable to be deflected inwardly through contact with a second wall defining the selected one of the apertures in the first plate.

5. The guide device of claim 4, wherein the second projection comprises a first end, a second end, and a curved portion, wherein the first end of the second projection engages with the first corner of the body and the curved portion of the second projection extends between the first and second ends of the second projection.

6. The guide device of claim 5, wherein the positioning of the first projection and the second projection provides a gap between the second ends of the first and second projections.

7. The guide device of claim 6, wherein the first and second projections are configured such that inward deflection of either of the first or second projections decreases the size of the gap.

8. The guide device of claim 1, wherein the first projection extends along the first generally lateral side of the body.

9. The guide device of claim 8, wherein the first projection is flush with the first generally lateral side of the body when the first projection is deflected inwardly.

10. The guide device of claim 1, wherein the first projection is pivotable relative to the body to deflect inwardly.

11. A guide device insertable into a grid plate for guiding a medical instrument relative to a patient, the guide device comprising:
   a. a body defined by a plurality of faces;
   b. at least one passageway, wherein the at least one passageway extends from a first face of the plurality of faces through the body to a second face of the plurality of faces, wherein the at least one passageway is configured to receive at least a portion of the medical instrument; and
   c. a first projection extending outwardly relative to the body, wherein the first projection is resiliently biased to extend outwardly relative to the body, wherein the first projection is inwardly deflectable through contact with the grid plate to securably and removably fit the guide device in the grid plate.

12. The guide device of claim 11, wherein the body further defines a first corner, wherein the first projection is located at the first corner.

13. The guide device of claim 12, wherein the first projection comprises a first end, a second end, and a curved portion, and wherein the first end of the first projection engages with the first corner of the body and the curved portion of the first projection extends between the first and second ends of the first projection.

14. The guide device of claim 13, further comprising a second projection extending from the body, wherein the second projection is inwardly deflectable through contact with a first wall defining the selected one of the apertures in the first plate, wherein the second projection comprises a first end, a second end, and a curved portion, wherein first end of the second projection is located at the first corner, wherein the curved portion of the second projection extends between the first and second ends of the second projection.

15. The guide device of claim 14, wherein the positioning of the first projection and the second projection provides a gap between the second ends of the first and second projections, wherein the gap is sized and configured to permit the first and second projections to deflect inwardly toward each other.

16. The guide device of claim 15, wherein first and second projections are configured such that the inward deflection of either of the first or second projections decreases the size of the gap.

17. The guide device of claim 11, wherein the body is further defined by a third face extending between the first and second faces, wherein the first projection extends along the third face of the plurality of faces of the body.

18. The guide device of claim 17, wherein the first projection is generally planar and includes a curvature that extends outwardly from the third face of the plurality of faces of the body.

19. The guide device of claim 18, wherein the first projection is pivotable relative to the third face to deflect inwardly.

20. A method of using a guide device to guide a medical instrument relative to a patient, wherein the guide device comprises a distal portion, a proximal portion, an internal passageway extending from the proximal portion to the distal portion, and at least one deflectable projection, the method comprising:
   a. positioning a grid plate adjacent to the patient, wherein the grid plate defines a plurality of apertures;
   b. inserting the distal portion of the guide device distally into a selected aperture of the grid plate, wherein the at least one deflectable projection resiliently bears against the grid plate upon insertion of the guide device into the selected aperture to securably and removably fit the guide device in the selected aperture; and
   c. inserting a portion of the medical instrument distally into the internal passageway, wherein the guide device guides the medical instrument into the patient as the medical instrument is inserted distally into the internal passageway of the guide device.

* * * * *